United States Patent
Harada

(10) Patent No.: US 7,629,598 B2
(45) Date of Patent: *Dec. 8, 2009

(54) PARTICLE BEAM IRRADIATION METHOD USING DEPTH AND LATERAL DIRECTION IRRADIATION FIELD SPREAD AND PARTICLE BEAM IRRADIATION APPARATUS USED FOR THE SAME

(75) Inventor: Hisashi Harada, Tokyo (JP)

(73) Assignee: Mitsubishi Denki Kabushiki Kaisha, Chiyoda-Ku, Tokyo (JP)

(*) Notice: Subject to any disclaimer, the term of this patent is extended or adjusted under 35 U.S.C. 154(b) by 230 days.

This patent is subject to a terminal disclaimer.

(21) Appl. No.: 11/632,910

(22) PCT Filed: Feb. 4, 2005

(86) PCT No.: PCT/JP2005/001709

§ 371 (c)(1),
(2), (4) Date: Jan. 19, 2007

(87) PCT Pub. No.: WO2006/082650

PCT Pub. Date: Aug. 10, 2006

(65) Prior Publication Data

US 2007/0295910 A1  Dec. 27, 2007

(51) Int. Cl.
  *G21K 5/04* (2006.01)
  *H01J 37/09* (2006.01)
  *A61N 5/00* (2006.01)

(52) U.S. Cl. ............... 250/492.3; 250/492.1; 250/503.1; 250/493.1; 250/505.1; 600/411; 315/501; 315/502; 315/503; 315/505

(58) Field of Classification Search ............... 250/492.1, 250/492.3, 503.1, 493.1, 505.1; 600/411, 600/407, 413, 410, 414, 415, 421, 436; 315/503, 315/501, 502, 505; 378/64, 65, 69, 145, 378/156, 137, 158, 159
See application file for complete search history.

(56) References Cited

U.S. PATENT DOCUMENTS 5,267,294 A * 11/1993 Kuroda et al. ................. 378/65

(Continued)

FOREIGN PATENT DOCUMENTS

DE  19907098  8/2000
JP  2004-358237  12/2004

OTHER PUBLICATIONS

Office Action (English-language translation) dated Mar. 10, 2009 issued in corresponding German Patent Application No. 11 2005 002 154.8-54, (4 pages).

(Continued)

*Primary Examiner*—Jack I Berman
*Assistant Examiner*—Nicole Ippolito Rausch
(74) *Attorney, Agent, or Firm*—Buchanan Ingersoll & Rooney PC

(57) ABSTRACT

In a particle beam irradiation method and a particle beam irradiation apparatus in which depth direction irradiation field spread and lateral direction irradiation field spread are performed, an irradiation dose in each of the irradiation layers of an irradiation target is made substantially constant, the control is simplified, and the irradiation error by the displacement of the irradiation target is reduced. The depth direction irradiation field spread is an active irradiation field spread to superimpose plural irradiation layers having different ranges in the irradiation direction of the particle beam. A bolus having a shape along a deepest part of the irradiation target in the depth direction is disposed to cross the particle beam. At least one irradiation layer selected from the plural irradiation layers is re-irradiated one or more times with the particle beam.

15 Claims, 15 Drawing Sheets

U.S. PATENT DOCUMENTS

| | | | |
|---|---|---|---|
| 5,969,367 A * | 10/1999 | Hiramoto et al. | 250/492.3 |
| 6,034,377 A | 3/2000 | Pu | |
| 6,246,066 B1 | 6/2001 | Yuehu | |
| 6,256,691 B1 | 7/2001 | Moroz et al. | |
| 6,307,914 B1 * | 10/2001 | Kunieda et al. | 378/65 |
| 6,316,776 B1 | 11/2001 | Hiramoto et al. | |
| 6,936,832 B2 * | 8/2005 | Norimine et al. | 250/505.1 |
| 6,984,835 B2 | 1/2006 | Harada | |
| 2001/0022502 A1 | 9/2001 | Akiyama et al. | |
| 2003/0160189 A1 | 8/2003 | Matsuda | |
| 2004/0092815 A1 * | 5/2004 | Schweikard et al. | 600/425 |
| 2004/0227104 A1 * | 11/2004 | Matsuda et al. | 250/492.1 |
| 2004/0267113 A1 * | 12/2004 | Thomson | 600/427 |
| 2007/0053484 A1 * | 3/2007 | Chiba et al. | 378/16 |

OTHER PUBLICATIONS

W.T. Chu et al., Instrumentation for treatment of cancer using proton and light-ion beams. Review of Scientific Instruments, Aug. 1993, pp. 2055-2096, 64 (8).

E. Pedroni et al., The 200-Mev proton therapy project at the Paul Scherrer Institute: Conceptual design and practical realization. Medical Physics, Jan. 1995, p. 37-53, 22 (1).

E. Pedroni, Paul Scherrer Institute Europhsics News (2000) vol. 31, No. 6.

* cited by examiner

PRIOR ART

FIG. 6
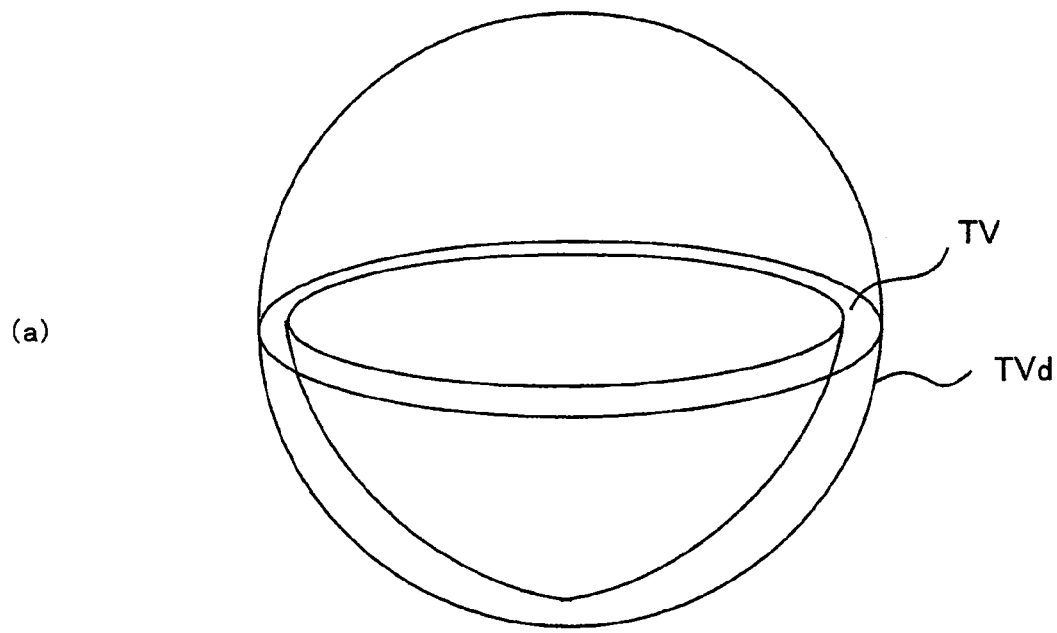
(a)
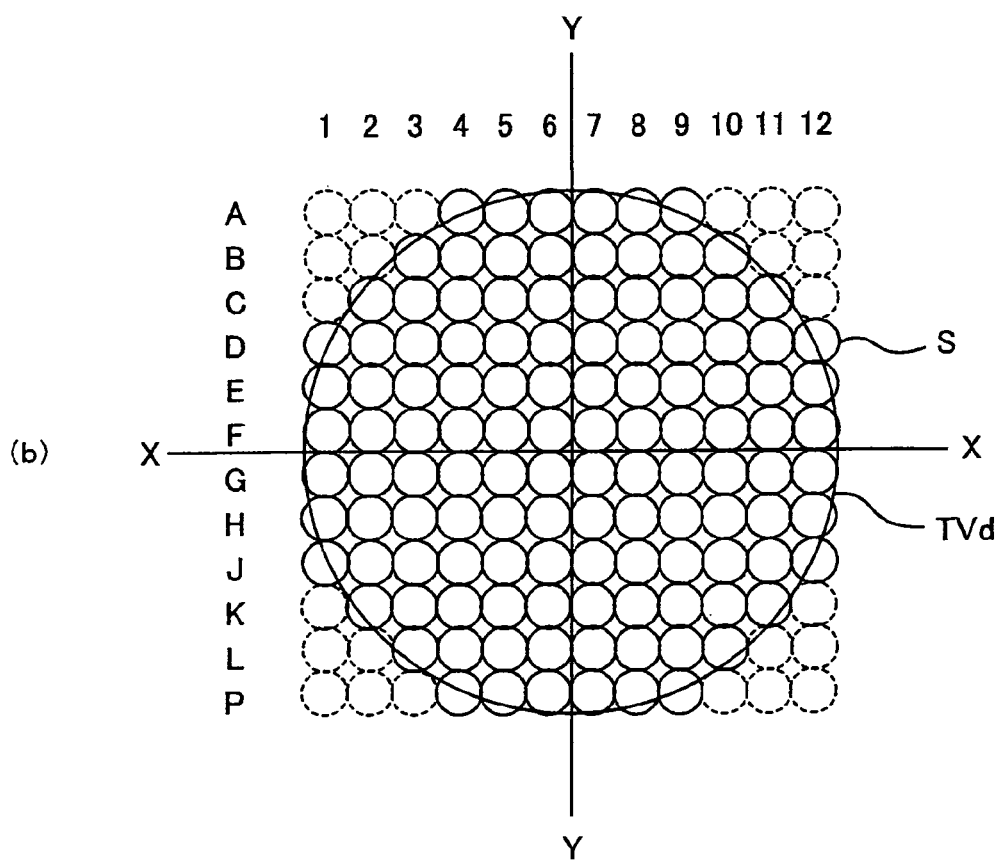
(b)

FIG. 7
(a)
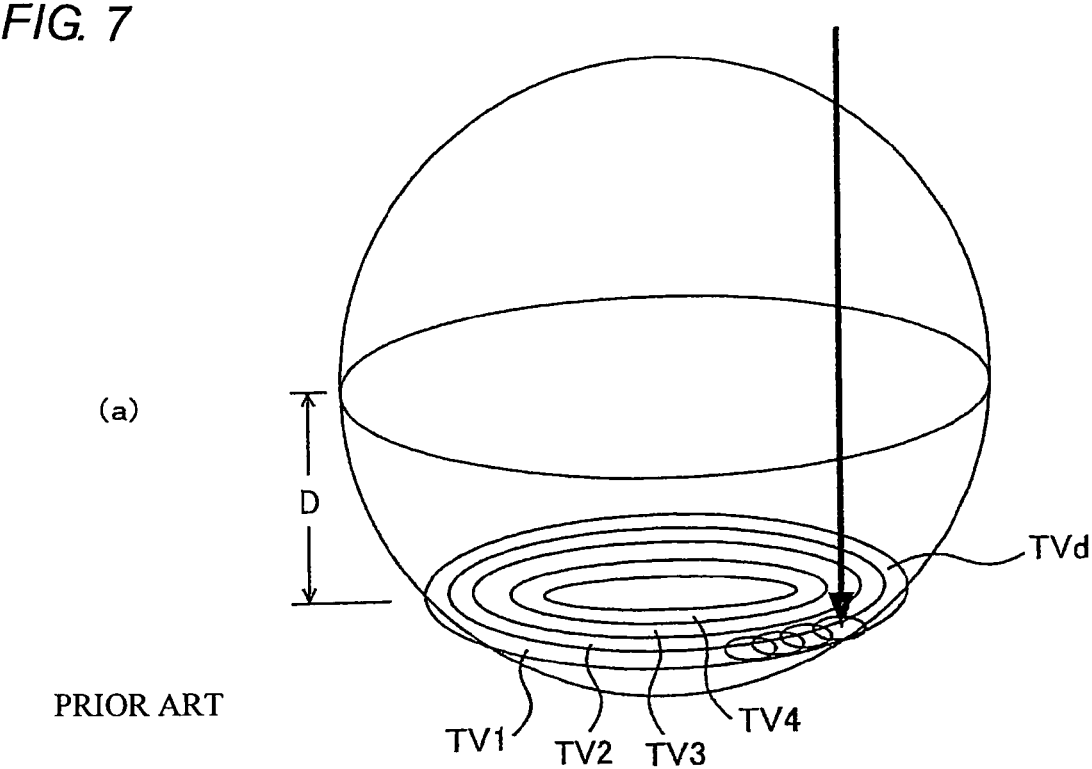
PRIOR ART
(b)
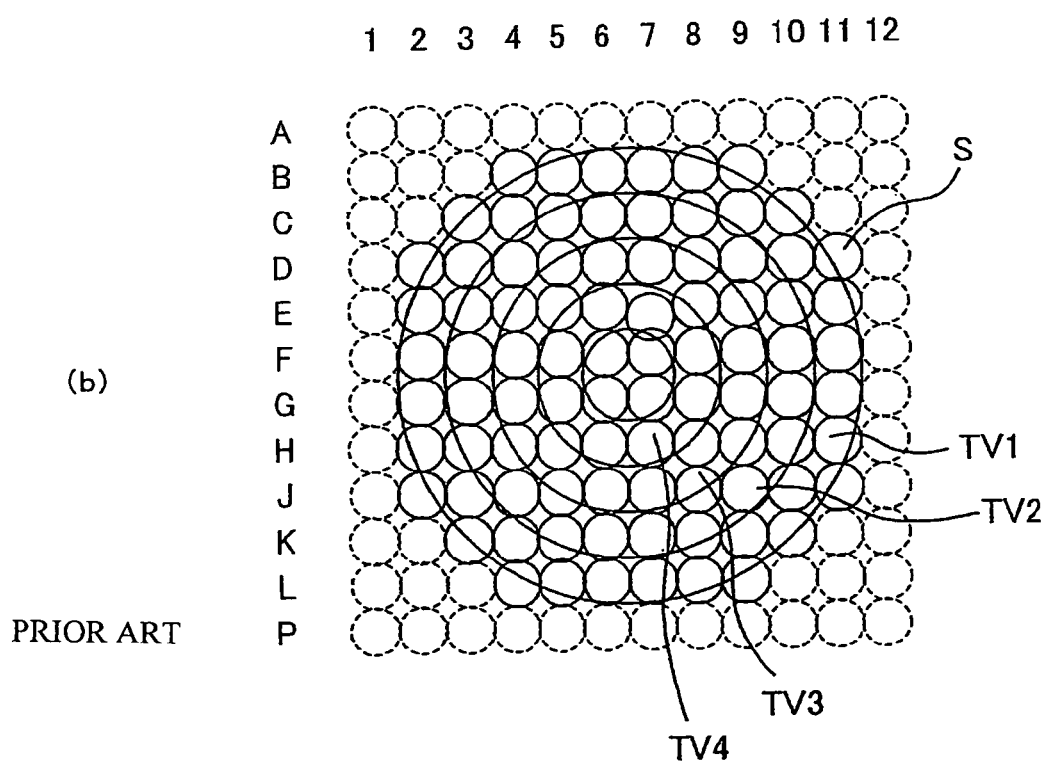
PRIOR ART

|  | ORDER OF IRRADIATION | | | | |
|---|---|---|---|---|---|
|  | FIRST | SECOND | THIRD | FOURTH | FIFTH |
| DEEPEST LAYER | 1 | 10 | 11 | 12 | 13 |
| SECOND LAYER | 2 | | | | |
| THIRD LAYER | 3 | | | | |
| FOURTH LAYER | 4 | | | | |
| FIFTH LAYER | 5 | | | | |
| SIXTH LAYER | 6 | | | | |
| SEVENTH LAYER | 7 | | | | |
| EIGHTH LAYER | 8 | | | | |
| NINTH LAYER | 9 | | | | |

FIG. 12

|  | ORDER OF IRRADIATION | | | | |
| --- | --- | --- | --- | --- | --- |
|  | FIRST | SECOND | THIRD | FOURTH | FIFTH |
| DEEPEST LAYER | 1 | 10 | 13 | 15 | 16 |
| SECOND LAYER | 2 | 11 | 14 | | |
| THIRD LAYER | 3 | 12 | | | |
| FOURTH LAYER | 4 | | | | |
| FIFTH LAYER | 5 | | | | |
| SIXTH LAYER | 6 | | | | |
| SEVENTH LAYER | 7 | | | | |
| EIGHTH LAYER | 8 | | | | |
| NINTH LAYER | 9 | | | | |

FIG. 13

|  | ORDER OF IRRADIATION | | | | |
| --- | --- | --- | --- | --- | --- |
|  | FIRST | SECOND | THIRD | FOURTH | FIFTH |
| DEEPEST LAYER | 1 | 10 | 11 | 12 | 13 |
| SECOND LAYER | 2 | 14 | 15 | | |
| THIRD LAYER | 3 | 16 | | | |
| FOURTH LAYER | 4 | | | | |
| FIFTH LAYER | 5 | | | | |
| SIXTH LAYER | 6 | | | | |
| SEVENTH LAYER | 7 | | | | |
| EIGHTH LAYER | 8 | | | | |
| NINTH LAYER | 9 | | | | |

FIG. 14

| | WEIGHTING (RELATIVE VALUE) | ORDER OF IRRADIATION | | | | | | | | | |
|---|---|---|---|---|---|---|---|---|---|---|---|
| | | FIRST | SECOND | THIRD | FOURTH | FIFTH | SIXTH | SEVENTH | EIGHTH | NINTH | TENTH |
| DEEPEST LAYER | 100 | 1 | 10 | 15 | 18 | 19 | 20 | 21 | 22 | 23 | 24 |
| SECOND LAYER | 30 | 2 | 11 | 16 | — | — | — | — | — | — | — |
| THIRD LAYER | 28 | 3 | 12 | 17 | — | — | — | — | — | — | — |
| FOURTH LAYER | 22 | 4 | 13 | — | — | — | — | — | — | — | — |
| FIFTH LAYER | 20 | 5 | 14 | — | — | — | — | — | — | — | — |
| SIXTH LAYER | 10 | 6 | 15 | — | — | — | — | — | — | — | — |
| SEVENTH LAYER | 8 | 7 | — | — | — | — | — | — | — | — | — |
| EIGHTH LAYER | 5 | 8 | — | — | — | — | — | — | — | — | — |
| NINTH LAYER | 5 | 9 | — | — | — | — | — | — | — | — | — |

FIG. 15

| | WEIGHTING (RELATIVE VALUE) | ORDER OF IRRADIATION | | | | | | | | | |
|---|---|---|---|---|---|---|---|---|---|---|---|
| | | FIRST | SECOND | THIRD | FOURTH | FIFTH | SIXTH | SEVENTH | EIGHTH | NINTH | TENTH |
| DEEPEST LAYER | 100 | 1 | 10 | 11 | 12 | 13 | 14 | 15 | 16 | 17 | 18 |
| SECOND LAYER | 30 | 2 | 19 | 20 | — | — | — | — | — | — | — |
| THIRD LAYER | 28 | 3 | 21 | 22 | — | — | — | — | — | — | — |
| FOURTH LAYER | 22 | 4 | 23 | — | — | — | — | — | — | — | — |
| FIFTH LAYER | 20 | 5 | 24 | — | — | — | — | — | — | — | — |
| SIXTH LAYER | 10 | 6 | — | — | — | — | — | — | — | — | — |
| SEVENTH LAYER | 8 | 7 | — | — | — | — | — | — | — | — | — |
| EIGHTH LAYER | 5 | 8 | — | — | — | — | — | — | — | — | — |
| NINTH LAYER | 5 | 9 | — | — | — | — | — | — | — | — | — |

PARTICLE BEAM IRRADIATION METHOD USING DEPTH AND LATERAL DIRECTION IRRADIATION FIELD SPREAD AND PARTICLE BEAM IRRADIATION APPARATUS USED FOR THE SAME

TECHNICAL FIELD

The present invention relates to a particle beam irradiation method applied to the treatment of a cancer or the like, and a particle beam irradiation apparatus used for the same.

BACKGROUND ART

As the related art relating to this kind of particle beam irradiation method and particle beam irradiation apparatus, the following two papers are known. The first paper is the paper titled "Instrumentation for treatment of cancer using proton and light-ion beams", by W. T. Chu, et al., printed in the magazine "Review of Scientific Instruments", 64(8), pp. 2055 to 2096, issued on August 1993.

The second paper is the paper titled "The 200-MeV proton therapy project at the Paul Scherrer Institute: Conceptual design and practical realization", by E. Pedoroni, et al., printed in the magazine "Medical Physics", 22(1), pp. 37-53, issued on January 1995.

The first paper describes that in the case where various radiation beams are transformed into thin diameter beams called pencil beams and are irradiated to a human body, the dose distributions of the radiation beams in the body are changed as shown in FIG. 1. As shown in FIG. 1, among various radiations, a radiation beam with a small mass, such as an X-ray or a gamma ray, has a relative dose which becomes maximum in a portion close to the surface of the body, and is decreased as the depth from the surface of the body is increased. On the other hand, a particle beam with a large mass, such as a proton beam or a carbon beam, has a relative dose which has a peak value at a position where the beam stops at a deep portion from the surface of the body, that is, immediately before the range of the particle beam. This peak value is called the Bragg Peak (BP).

A particle beam cancer treatment method is such that this Bragg peak BP is irradiated to a tumor formed in a human organ and the treatment of the cancer is performed. In addition to the cancer, it can also be used for a case where a deep portion of a body is treated. A region to be treated, including a tumor, is generally called an irradiation target. The position of the Bragg peak is determined by the energy of an irradiated particle beam, and as the energy of the particle beam becomes high, the Bragg peak BP is formed at a deep position. In the particle beam treatment, it is necessary that the particle beam is made to have a uniform dose distribution over the whole of the irradiation target to be irradiated. In order to give the Bragg peak BP to the whole area of the irradiation target, "spread of irradiation field (radiation field)" of the particle beam is performed.

This "spread of irradiation field" is performed in three directions of an X-axis, a Y-axis and a Z-axis perpendicular to each other. When the irradiation direction of the particle beam is made the direction of the Z-axis, the "spread of irradiation field" is first performed in the Z-axis direction. The "spread of irradiation field" in the irradiation direction of the radiation beam is generally called depth direction irradiation field spread. The second "spread of irradiation field" is such that the irradiation field spread is performed in the X-axis and Y-axis directions, and since the irradiation field spread is performed in the lateral direction perpendicular to the depth direction, it is generally called lateral direction irradiation field spread.

The depth direction irradiation field spread is performed to spread the Bragg peak, which is in the irradiation direction of the particle beam, in the depth direction since the width of the Bragg peak BP in the irradiation direction of the particle beam is narrow as compared with the extent of the irradiation target in the depth direction. On the other hand, the lateral direction irradiation field spread is performed to spread the Bragg peak BP in the direction perpendicular to the irradiation direction since the diameter of the particle beam is smaller than the size of the irradiation target in the direction perpendicular to the irradiation direction. With respect to the depth direction irradiation field spread and the lateral direction irradiation field spread, methods described in the respective foregoing papers will be described.

First, the lateral direction irradiation field spread includes a passive lateral direction irradiation field spread method and an active lateral direction irradiation field spread method. The passive lateral direction irradiation field spread method is a method in which in a particle beam irradiation part of a particle beam irradiation apparatus, a particle beam is irradiated to a scatterer to cause the particle beam to have an extent in the lateral direction, and a uniform dose portion of the center portion is cut out and is irradiated to the target region. In the case where the uniform dose portion can not be made sufficiently large by one scatterer, there is a case where the uniform dose portion is spread by two scatterers, and this is called a double scatterer method. Besides, there is also a method in which two deflection electromagnets provided at the upstream portion of a particle beam irradiation part of a particle beam irradiation apparatus are used to scan the particle beam in a doughnut shape, and the particle beam scanned in the doughnut shape is irradiated to the scatterer to spread the lateral direction irradiation field, and this is called a Wobbler System.

As the active lateral direction irradiation field spread method, there is a method in which a deflection electromagnet provided at the upstream portion of a particle beam irradiation part of a particle beam irradiation apparatus is used to scan the particle beam in the XY plane, and the irradiation position of the particle beam is moved with the lapse of time to obtain a wide irradiation field. In this method, a uniform dose distribution can be obtained by suitably overlapping adjacent irradiation spots of thin diameter pencil beams. Scanning methods of pencil beams include a raster method of performing scanning continuously with respect to time, and a spot method of performing a step-like scanning with respect to time. Incidentally, in this method, although the particle beam is generally called a pencil beam having a thin diameter and is directly irradiated to the target region, there is also a case where the diameter of the pencil beam is slightly enlarged by using a thin scatterer.

Next, the depth direction irradiation field spread will be described. As described before, the width of the Bragg peak BP in the irradiation direction of the particle beam is narrow, and the width of the Bragg peak BP in the irradiation direction is spread by the depth direction irradiation field spread. The Bragg peak BP in which the width in the irradiation direction is spread is called spread-out Bragg peak. First, the depth direction passive irradiation field spread method includes a method in which a comb-type energy modulator called a ridge filter or a range modulator is inserted so as to cross the particle beam.

In both the ridge filter and the range modulator, the thickness of the material of the energy modulator is modulated in the irradiation direction of the particle beam. The ridge filter or the range module decreases the energy of the particle beam according to the modulated thickness, and changes the energy according to the modulated thickness, and consequently, the particle beam in which various energies with different intensities are mixed is irradiated to the irradiation target. Since the range of the particle beam is changed according to the intensity of the energy, the particle beam having various ranges can be irradiated to the irradiation target. In the passive depth direction irradiation field spread method as stated above, the spread-out Bragg peak SOBP in which the width is spread in the irradiation direction can be obtained. However, the width of the spread-out Bragg peak SOBP is constant in the lateral direction, that is, in the directions of the X and Y axes perpendicular to the irradiation direction of the particle beam, and it can not be changed.

As another depth direction passive irradiation field spread method, there is a method in which a compensator called a bolus is used. In general, a region to be treated in a patient is positioned at the maximum depth of an affected organ in the depth direction, that is, at the deepest part (boundary of the affected organ in the depth direction) of the affected organ in the Z-axis direction, and in general, the depth of the region to be treated has dependency in the lateral direction (X, Y-axis direction), and is changed in the X-axis and Y-axis directions. The change shape of the region to be treated in the depth direction is called a distal shape. As shown in FIG. 2, the bolus BL is an energy modulator which is fabricated for each patient in conformity with this distal shape, and is formed by using polyethylene or wax. By using the bolus BL, while the uniform irradiation dose is irradiated to the X, Y plane, the Bragg peak BP can be conformed to the distal shape.

FIG. 2(a) shows an irradiation target TV and a bolus BL. The irradiation target TV has the deepest layer TVd, and the shape of the deepest layer TVd is called the distal shape. Seven arrows indicate typical particle beams. In FIG. 2(b), the doses of the seven typical particle beams to the irradiation target TV are indicated by a to g. By using the bolus BL, the dose distribution in the deepest layer TVd can be flattened.

As the depth direction active irradiation field spread method, there is a method in which the energy of the particle beam itself irradiated from a particle beam irradiation apparatus is controlled, while the foregoing energy modulator is not used. In this method, the energy of the particle beam is controlled by changing the acceleration energy of an accelerator to accelerate the particle beam, or the energy of the particle beam is changed by inserting a tool called a range shifter so as to cross the particle beam. There is also a method in which both the control of the accelerator and the range filter are used.

In the depth direction active irradiation field spread method, the particle beam is a beam having the energy of specified intensity, and after the Bragg peak BP with a uniform dose is irradiated to an irradiation layer of the irradiation target, the energy of the particle beam is changed, and the Bragg peak BP is irradiated to the irradiation layer next to the irradiation target TV. Such operation is repeated plural times, and the Bragg peak BP of the particle beam is irradiated to the plural irradiation layers, so that the spread-out Bragg peak SOBP having a desired width in the beam irradiation direction can be obtained. The depth direction active irradiation field spread method is a method in which, in the state where the particle beam is not moved in the X and Y-axis directions and is fixed to a definite irradiation position, the energy of the particle beam is changed.

In order to obtain the spread-out Bragg peak SOBP having the desired width, it is necessary to suitably adjust the dose of each irradiation layer of the irradiation target TV, and the dose given to each layer is called "weighting of layer". This "weighting of layer" is calculated by the same method as the ridge filter or the range module. FIG. 3 shows an example of the dose distribution in the depth direction and the "weighting of layer". In FIG. 3, the vertical axis indicates the relative dose, and the horizontal axis indicates the depth in the body. A curved line indicated by a solid line indicates calculated values, and plural small squares indicate actually measured values. Plural straight lines extending in the vertical direction indicate the weightings in the respective irradiation layers. This example is a typical example, and the "weighting of layer" is highest at the deepest part. When the weighting of the deepest part is 100, the weighting of the layer adjacent thereto is almost 10 or less.

A particle beam irradiation method in which the depth direction active irradiation field spread and the lateral direction active irradiation field spread are combined is described as a spot scanning technique on page 39 to page 45 of the document 2. This spot scanning technique is a method in which while the particle beam is scanned on the X, Y plane by the active lateral direction irradiation field spread, the irradiation dose of the particle beam is changed by the active depth direction irradiation field spread, and the Bolus is not used.

Besides, a particle beam irradiation method in which the depth direction active irradiation field spread method and the lateral direction passive irradiation field spread method are combined is described as a three-dimensional irradiation system on page 2092, left column, line 6 from the bottom to the same page, right column, line 2 of the foregoing first paper. In this three-dimensional irradiation system, the bolus is also used.

Non-patent document 1: paper titled "Instrumentation for treatment of cancer using proton and light-ion beams", by W. T. Chu, et al., printed in the magazine "Review of Scientific Instruments", 64(8), pp. 2055 to 2096, issued on August 1993.

Non-patent document 2: paper titled "The 200-MeV proton therapy project at the Paul Scherrer Institute: Conceptual design and practical realization", by E. Pedoroni, et al., printed in the magazine "Medical Physics", 22(1), pp. 37-53, issued on January 1995.

DISCLOSURE OF THE INVENTION

Problems that the Invention is to Solve

However, in the spot scanning technique, with respect to each of the irradiation depths, the irradiation dose of the particle beam at each position of the X, Y plane is controlled. Thus, a portion with a high weighting and a portion with a low weighting are mixed at each of the irradiation depths, and the portion with the high weighting and the portion with the low weighting are changed at each of the irradiation depths. Accordingly, there is a disadvantage that the control becomes complicated.

On the other hand, in the three-dimensional irradiation system, the specified irradiation dose is spread at each position of the X, Y plane by the passive lateral direction irradiation field spread, and the uniform irradiation dose on the X, Y plane can be matched to the specified dose in the deepest layer TVd of the irradiation target, and therefore, the control becomes easy.

However, there is a problem that an irradiation target is displaced during irradiation by the breath of a patient, the blood flow or other physiological phenomena. With respect to the displacement of the irradiation target during the irradiation, in the spot scanning technique and the three-dimensional irradiation system, it is difficult to irradiate the irradiation target with the accurate irradiation dose. The displacement of the irradiation target becomes a problem especially when the lung, the liver or the like is treated, and there is a problem that a desired dose distribution can not be given to the respective irradiation layers. This problem causes a danger that the particle beam is irradiated to a portion other than the irradiation target determined by a treatment plan. Besides, there occurs a result that the superposition of the irradiation doses is not performed well, and the uniformity of the irradiation dose in the irradiation target can not be insured. Because of these problems, there are very few examples in which the spot scanning technique and the three-dimensional irradiation system are used for the treatment of cancer of the lung or the liver.

Means for Solving the Problems

A particle beam irradiation method of the invention is a particle beam irradiation method which uses both a depth direction irradiation field spread for spreading an irradiation field of a particle beam in a direction of a depth direction along an irradiation direction of an irradiation direction of the particle beam, and a lateral direction irradiation field spread for spreading the irradiation field of the particle beam in a lateral direction perpendicular to the irradiation direction of the particle beam, and irradiates the particle beam to an irradiation target. In the particle beam irradiation method, the depth direction irradiation field spread is an active irradiation field spread in which plural irradiation layers with different ranges are superimposed in the irradiation direction of the particle beam, a bolus having a shape along a deepest part of the irradiation target in the depth direction is disposed to cross the particle beam, and at least one irradiation layer selected from the plural irradiation layers is re-irradiated once or more with the particle beam.

Besides, a particle beam irradiation apparatus of the invention is a particle beam irradiation apparatus including a particle beam generation part for generating a particle beam, a particle beam transport part for transporting the particle beam generated by the particle beam generation part, a particle beam irradiation part for irradiating the particle beam transported by the particle beam transport part to an irradiation target, depth direction irradiation field spread means for spreading an irradiation field of the particle beam in a direction of a depth direction along an irradiation direction of an irradiation direction of the particle beam and lateral direction irradiation field spread means for spreading the irradiation field of the particle beam in a lateral direction perpendicular to the irradiation direction of the particle beam, In the particle beam irradiation apparatus, the depth direction irradiation field spread means is active depth direction irradiation field spread means for superimposing plural irradiation layers with different ranges in the irradiation direction of the particle beam, a bolus having a shape along a deepest part of the irradiation target in the depth direction is disposed to cross the particle beam, and at least one irradiation layer selected from the plural irradiation layers is re-irradiated once or more with the particle beam.

EFFECTS OF THE INVENTION

In the particle beam irradiation method of the invention, the depth direction irradiation field spread is the active irradiation field spread in which the plural irradiation layers with the different ranges are superimposed in the irradiation direction of the particle beam, and the bolus having the shape along the deepest part of the irradiation target in the depth direction is disposed to cross the particle beam, and therefore, the substantially uniform irradiation dose can be given to the deepest layer of the irradiation target in the depth direction by the relatively simple structure. Further, at least one irradiation layer selected from the plural irradiation layers is re-irradiated once or more with the particle beam, and therefore, even if the irradiation target is displaced, a more accurate irradiation dose can be given to the selected irradiation layer.

Besides, in the particle beam irradiation apparatus of the invention, the depth direction irradiation field spread means is the active depth direction irradiation field spread means in which the plural irradiation layers with the different ranges are superimposed in the irradiation direction of the particle beam, and the bolus having the shape along the deepest part of the irradiation target in the depth direction is disposed to cross the particle beam, and therefore, the substantially uniform irradiation dose can be given to the deepest layer of the irradiation target in the depth direction by the relatively simple structure. Further, at least one irradiation layer selected from the plural irradiation layers is re-irradiated once or more with the particle beam, and therefore, even if the irradiation target is displaced, a more accurate irradiation dose can be given to the selected irradiation layer.

BEST MODE FOR CARRYING OUT THE INVENTION

Hereinafter, some embodiments of the invention will be described with reference to the drawings.

Embodiment 1

First, embodiment 1 of the invention will be described. In this embodiment 1, the embodiment 1 of a particle beam irradiation apparatus of the invention will be described, and further, the embodiment 1 of a particle beam irradiation method of the invention will be described.

This embodiment 1 is characterized in that an active depth direction irradiation field spread and an active lateral direction irradiation field spread are combined, and in addition to these, a bolus having a shape of a deepest part of an irradiation target in a depth direction is used, and a deepest layer of plural irradiation layers is re-irradiated once or more.

First, the structure of the particle beam irradiation apparatus will be described. FIG. 4 shows the whole structure of the embodiment 1 of the particle beam irradiation apparatus used for carrying out the embodiment 1 of the particle beam irradiation method of the invention. As shown in FIG. 4, the embodiment 1 of the particle beam irradiation apparatus includes a particle beam generation part 10, a particle beam transport part 20, and three particle beam irradiation parts 30A, 30B and 30C. For reasons of application of radiation safety management and the like, the particle beam generation part 10 and the particle beam irradiation parts 30A, 30B and 30C are installed in individual shielded rooms. The particle beam transport part 20 connects the particle beam generation part 10 to the respective particle beam irradiation parts 30A, 30B and 30C. The acceleration particle beam transport part 20 includes particle beam transport passages 21, 22 and 23 to transport the particle beam generated in the particle beam generation part 10 to the particle beam irradiation parts 30A, 30B and 30C. The particle beam transport passages 21, 22 and 23 are constructed of vacuum ducts. The particle beam irradiation parts 30A, 30B and 30C irradiate the particle beam PB to a target region TV of a patient.

The particle beam generation part 10 includes an ion source 11 and an accelerator 12. The ion source 11 generates the particle beam with large mass, such as a proton beam or a carbon beam. The accelerator 12 accelerates the particle beam generated in the ion source 11, and forms the particle beam PB. This particle beam is formed as a pencil beam with a thin diameter. An energy setting controller 13 is electrically connected to the accelerator 12. The energy setting controller 13 supplies an energy control signal ES to the accelerator 12, sets and controls the acceleration energy of the particle beam PB by the accelerator 12, and constitutes active depth direction irradiation field spread means 15. The active depth direction irradiation field spread means 15 is controlled by a control calculator to control the whole apparatus, and performs a control to superimpose plural irradiation layers having different ranges in the depth direction. The irradiation energy of the particle beam is changed for each of the plural irradiation layers, and the spread-out Bragg peak SOBP is formed in the irradiation direction of the particle beam PB, that is, in the Z-axis direction.

The particle beam irradiation parts 30A, 30B and 30C constitute a treatment room 1, a treatment room 2, and a treatment room 3, respectively. The three particle beam irradiation parts 30A, 30B, and 30C have the same structure as one another, and each of them includes an irradiation nozzle 31, a treatment stand 32, and a positioning device 33. The treatment stand 32 is used for keeping a patient in the state of a dorsal position or a sitting position, and the positioning device 33 is used for confirming the position of an the affected organ by an X-ray apparatus or the like. The irradiation nozzle 31 irradiates the particle beam PB transported to the particle beam irradiation parts 30A, 30B, 30C to the irradiation target TV of the patient on the treatment stand 32.

FIG. 5 shows the specific structure of the irradiation nozzle 31 of the particle beam irradiation parts 30A, 30B and 30C in the embodiment 1. The irradiation nozzle shown in FIG. 5 is denoted by symbol 31A. The irradiation nozzle 31A shown in FIG. 5 includes deflection electromagnets 41a and 41b to scan the particle beam PB in a lateral direction, that is, on the X, Y plane perpendicular to the irradiation direction of the particle beam PB, beam position monitors 42a and 42b to monitor the irradiation position of the particle beam PB, a dose monitor 43 to monitor the irradiation dose of the particle beam PB, and a bolus attachment stand 44. A bolus 45 is attached to the bolus attachment stand 44.

An arrow PB of FIG. 5 indicates the irradiation direction of the particle beam PB. The deflection electromagnets 41a and 41b are disposed to be adjacent to each other at the upstream side in the irradiation direction. The beam position monitors 42a and 42b are disposed to be spaced from each other in the irradiation direction, and the dose monitor 43 is disposed between the beam position monitors 42a and 42b and near the beam position monitor 42b. The bolus attachment stand 44 is disposed nearest a patient and at the downstream side in the irradiation direction.

The deflection electromagnets 41a and 41b shown in FIG. 5 constitute lateral direction active irradiation field spread means 40 for spreading the Bragg peak BP of the particle beam PB in the lateral direction perpendicular to the irradiation direction. The lateral direction active irradiation field spread means 40 is controlled by a control calculator to control the whole apparatus, and forms the spread-out SOBP in the lateral direction perpendicular to the irradiation direction of the particle beam BP, that is, in the X-axis and Y-axis directions. Specifically, the particle beam PB is scanned in the lateral direction, that is, on the XY plane, and the spread-out SOBP is formed on the XY plane.

The bolus 45 attached to the bolus attachment stand 44 has a shape along the distal shape of a deepest part of an irradiation target TV, that is, a region to be treated. The bolus 45 is an energy modulator fabricated for each patient and is formed by using polyethylene or wax. The bolus 45 is disposed so as to cross the particle beam PB irradiated from the irradiation nozzle 31A to the irradiation target TV of the patient, and by using the bolus 45, the irradiation dose to the deepest layer TVd of the irradiation target TV and each of the irradiation layers adjacent thereto can be flattened on the X, Y plane.

The first feature of the embodiment 1 is that the active depth direction irradiation field spread means 15 and the active lateral direction irradiation field spread means 40 are combined with the bolus 45. The combination of the active depth direction irradiation field spread and the active lateral direction irradiation field spread is known as the spot scanning technique. In this embodiment 1, the bolus 45 is further combined therewith and is used. Also as shown in FIG. 3, layer weighting to plural irradiation layers is highest for the deepest layer TVd, and in the case where the weighting of the deepest layer TVd is made 100, the weighting of each of irradiation layers adjacent thereto is 1/5 or less. In this embodiment 1, by using the bolus 45, the irradiation dose to the deepest layer TVd of the irradiation target TV and each of the irradiation layers adjacent thereto can be flattened on the X, Y plane. Thus, although the irradiation dose of each of the irradiation layers is changed for the respective irradiation layers by the active depth direction irradiation field spread means 15, the irradiation dose at each position on the X, Y plane can be made substantially constant for each of the irradiation layers, and the control can be simplified. Although the energy control signal ES given to the accelerator 12 from the active irradiation field spread means 15 is changed for the respective irradiation layers, it is kept at a substantially constant value for each of the irradiation layers, and the control is simplified.

The irradiation method of the particle beam of the embodiment 1 will be described in contrast to the conventional spot scanning technique. FIGS. 6(a) and 6(b) show the irradiation method of the embodiment 1, and FIGS. 7(a) and 7(b) show the conventional spot scanning technique. FIG. 6(a) and FIG. 7(a) show the shapes of irradiation targets, and a semicircular irradiation target TV is supposed in each of them. A deepest layer TVd is a surface portion of this semicircular irradiation target TV. FIG. 8 shows the shape of the bolus 45 used for irradiation to the irradiation target TV shown in FIG. 6(a)(b).

FIG. 6(b) schematically shows the distribution of the particle beam PB to the deepest layer TV and on the X, Y plane according to the embodiment 1, and FIG. 7(b) schematically shows the distribution of the particle beam PB to the irradiation depth D and on the X, Y plane according to the conventional spot scanning technique. In FIG. 6(b) and FIG. 7(b), plural small circles S indicate irradiation spots each corresponding to the diameter of the particle beam PB. Although these irradiation spots are actually scanned such that the irradiation spots adjacent to each other are partially overlap with each other, for simplification of the drawings, they are shown in a state where there is no overlap. Besides, although the number of the irradiation spots S is actually larger, they are shown while the number is made smaller than an actual one.

In FIG. 6(b) and FIG. 7(b), the X-axis in the lateral direction relative to the particle beam PB is indicated by a line X-X, and the Y-axis is indicated by a line Y-Y. Addresses of from 1 to 12 are assigned along the line X-X, and addresses of from A to P are assigned along the line Y-Y. The deepest layer TVd of the irradiation target TV shown in FIG. 6(a) is indicated by a large circle TVd, and plural irradiation spots S in the inside of the circle TVd or partially overlapping with this circle TVd are indicated by small circles S of solid lines. These small circles S of the solid lines are the particle beams PB corresponding to the deepest layer TVd of the irradiation target TV.

In FIG. 6(b), the irradiation spots S are basically scanned from address A1 along the line X-X, a shift is made from address A12 to address B1, and scanning is performed to the final address P12. With respect to the deepest layer TVd, only the irradiation spots S indicated by the small circles of the solid lines are scanned with the same irradiation dose. The irradiation to the deepest layer TVd is achieved by scanning the irradiation spots S corresponding to the circle TVd while the same irradiation dose is held.

In the conventional spot scanning technique, since the bolus 45 is not used, with respect to the irradiation depth D (see FIG. 7(a)) of the same semicircular irradiation target TV, plural annular portions TV1 to TV 4 different in the irradiation dose are supposed as shown in FIGS. 7(a) and 7(b). In the case where the irradiation spot S is scanned to the annular portions TV1 to TV4, since, for example, addresses B6 and B7 correspond to the deepest layer TVd, it is necessary to make the irradiation dose high. However, since, for example, addresses C6 and C7 are shallower than the deepest layer TVd, the irradiation dose to be given is made small. In the line of address F, since addresses F2 and F11 correspond to the deepest layer TVd, the high irradiation dose is given. However, since addresses F3 and F10 correspond to the shallow layer adjacent to the deepest layer TVd, it is necessary to make the irradiation dose small. Besides, since addresses F4 and F9 are further shallow layers adjacent to the addresses F3 and F10 when viewed from the deepest layer TVd, it is necessary to further make the irradiation dose small.

As stated above, in the conventional spot scanning technique, with respect to the irradiation depth D, when the X, Y plane is scanned, it is necessary to frequently change the irradiation dose. With respect to the irradiation dose, the beam current is changed in the accelerator 12 by the depth direction irradiation field spread means 15, however, it is difficult to perform the frequent change of the beam current without error.

As an active lateral direction irradiation field spread method, in the case where a spot method is adopted in which the particle beam PB is scanned stepwise, the irradiation dose given to each irradiation spot S is controlled by the irradiation time. The control device of the irradiation dose has values of planned dose corresponding to the respective irradiation spots S in a tabular form, and the particle beam of each irradiation spot S is temporarily stopped at the time point when the irradiation dose reaches the planned dose. Although the irradiation dose can be controlled by the irradiation time as stated above, in order to accurately control the irradiation dose, the accelerator 12 supplies the beam current suitable for the planned dose of the irradiation spot and further, the beam current must be accurately controlled.

In the control of the beam current of the accelerator 12 as stated above, in the conventional spot scanning technique, the beam current is made large in the portions corresponding to the deepest layer TVd, such as the addresses F2 and F11 of FIG. 7(b), and the beam current is sequentially made small in the addresses F3 and F10 and the addresses F4 and F9. However, since the adjustment of the beam current of the accelerator 12 can not be instantaneously performed, in order to change the beam current with respect to the certain depth D, it is necessary to prolong the irradiation time, and there is a problem that the control becomes complicated.

On the other hand, like the embodiment 1, when the active depth direction irradiation field spread means 15 and the active lateral direction irradiation field spread means 40 are combined with the bolus 45, the irradiation dose to be given to the irradiation spot S can be kept substantially constant in the deepest layer TVd and each of the irradiation layers adjacent thereto, and the beam current of the accelerator 12 can be kept substantially constant with respect to each of the irradiation layers. Thus, the control can be simplified.

In the embodiment 1, as the second feature, the deepest layer TVd in the respective irradiation layers of the irradiation target TV is re-irradiated once or more with the particle beam PB. Since the irradiation dose to be given to the deepest layer TVd is 5 to 20 times as large as that of the other irradiation layer, when the irradiation dose to the deepest layer TVd is made accurate, the accuracy of the whole irradiation dose distribution can be improved.

In the embodiment 1, the particle beam PB is irradiated in the irradiation procedure shown in FIG. 9. This control procedure is stored in a storage device of a control calculator to control the whole apparatus. In FIG. 9, the respective irradiation layers of from the deepest layer TVd to the second layer, the third layer, . . . , the ninth layer are arranged along the vertical column, the sequence of irradiations of the first, the second, . . . , the fifth is arranged in the horizontal column, and irradiation sequences are written as 1, 2, 3, . . . , 13 at the intersection points of the respective irradiation layers and the respective sequence of irradiations. The irradiation of the particle beam PB is executed in order of the irradiation sequences 1, 2, 3, . . . , 13.

In the irradiation procedure of FIG. 9, the first irradiation includes the irradiation of the irradiation sequence 1 to the deepest layer TVd, and the irradiations of the irradiation sequences 2, 3, 4, 5, 6, 7, 8 and 9 to the respective layers of from the second layer to the ninth layer. The second irradiation includes the irradiation of the irradiation sequence 10 to the deepest layer TVd, the third irradiation includes the irradiation of the irradiation sequence 11 to the deepest layer TVd, and the fourth and fifth irradiations respectively include the irradiations of the irradiation sequences 12 and 13 to the deepest layer TVd. All the irradiations of the irradiation sequences 10, 11, 12 and 13 are reirradiations to the deepest layer TVd.

Each of the five irradiations of the irradiation sequences 1, 10, 11, 12 and 13 to the deepest layer TVd is performed with a dose of ⅕ of the highest irradiation dose RV1 corresponding to the deepest layer TVd, and the total irradiation dose becomes RV1. Irradiation doses RV2 to RV9 to the layers of from the second layer to the ninth layer are sequentially decreased from the irradiation dose RV1. In FIG. 9, the number of times of irradiation to the deepest layer TVd is made five, the necessary irradiation dose RV1 is divided into five equal parts, and the five irradiations are performed with an irradiation dose of RV/5.

FIGS. 10(a), 10(b), 10(c) and 10(d) are diagrams showing the improvement situation of the error of an irradiation dose due to the displacement of the irradiation target TV in the case where the number of times of irradiation to the deepest layer TVd is two in total, that is, the number of times of reirradiation is 1.

In FIG. 10(a), the irradiation target TV is denoted by symbol 101, and it is assumed that the irradiation target TV is displaced with breath in the direction of an arrow B along a horizontal axis 206. In FIG. 10(b), the first distribution of an irradiation dose to the deepest layer TVd is indicated by a solid line curve 201, and the second distribution of an irradiation dose to the deepest layer TVd is indicated by a dotted line curve 202. FIG. 10(c) shows the first distribution 201 of the irradiation dose, and a curve 203 of the distribution of the total irradiation dose in which the first and the second irradiation doses are added.

In FIG. 10(d), the distribution of an irradiation dose in a case where the irradiation to the deepest layer TVd is executed only once is indicated by a curve 205, and the curve 205 and the curve 203 are compared with each other. A gray flow area 204 of FIG. 10(d) indicates an area of the curve 205 where an irradiation dose larger than the curve 203 is given by the displacement of the irradiation target TV.

As stated above, in the case where the irradiation is performed only once to a certain irradiation layer such as the deepest layer TVd, there is a danger that an excessive irradiation dose is given by the displacement of the irradiation target TV in the area 204. However, by the reirradiation, division is made into plural parts, and when the irradiation is performed with the equally divided irradiation dose, the occurrence of the excessive irradiation area 204 can be prevented.

In the example of FIG. 10, for simplifying the explanation, there is used a distribution in which the dose is decreased linearly from 100% to 0% at both ends of the curves 201, 202, 203 and 205 of the dose distribution. Actually, although the end of the dose distribution is close to the convoluted function of the Gaussian distribution, this explanation does not depend on a specific mathematical expression. When the number of times of irradiation to the deepest layer TVd is further increased, the dose distribution is further improved. Also with respect to the depth direction, similarly, when the irradiation is performed plural times, the irradiation distribution can be improved.

In the conventional spot scanning technique in which the active depth direction irradiation field spread and the active lateral direction irradiation field spread are combined, since the bolus 45 is not used, as shown in FIGS. 7(a) and 7(b), the deepest layer TVd exists only at the outer peripheral part of each of the irradiation layers in which the irradiation depth D (see FIG. 7(a)) is changed. Thus, in the conventional spot scanning technique, in order to re-irradiate the deepest layer TVd, the reirradiation is required to be performed with respect to many irradiation layers, and the energy of the accelerator 12 is required to be adjusted with respect to the respective irradiation layers in which the irradiation depth D is changed, and the complicated control is required.

In the embodiment 1, since the bolus 45 is used, as shown in FIG. 6(b), the deepest layer TVd can be concentrated into one layer, and the adjustment of energy of the accelerator 12 is unnecessary in the irradiation of the deepest layer TVd, and therefore, the whole deepest layer TVd can be easily re-irradiated.

As stated above, according to the embodiment 1, also with respect to the irradiation target TV which is displaced based on the physiological activity, such as breadth, of the patient, while the irradiation accuracy of the irradiation spot S is held, it is possible to prevent the irradiation time from being prolonged.

As stated above, in the embodiment 1, the deepest layer TVd is re-irradiated once or more, and the number of times of irradiation is made plural, so that the error of the irradiation dose by the displacement of the target region TV can be reduced.

Incidentally, the dose distribution and the specific numerical values of the weighting described here are an example, and the effect of the invention does not depend on the specific numerical values.

Embodiment 2

Next, embodiment 2 of the invention will be described. Also in the embodiment 2, the embodiment 2 of a particle beam irradiation apparatus of the invention will be described, and further, the embodiment 2 of a particle beam irradiation method of the invention will be described.

The embodiment 2 is characterized in that an active depth direction irradiation field spread and a passive lateral direction irradiation field spread are combined, and further, a bolus 45 is combined and is used, and reirradiation is performed once or more to a deepest layer TVd of an irradiation target.

In the particle beam irradiation apparatus of the embodiment 2, instead of the active lateral direction irradiation field spread means 40 in the particle beam irradiation apparatus of the embodiment 1, passive lateral direction irradiation field spread means 50 is used. Besides, in the embodiment 2, in addition to the active depth direction irradiation field spread means 15, active depth direction irradiation field spread means 60 is added. The particle beam irradiation apparatus of the embodiment 2 is constructed similarly to the embodiment 1 except the above.

In the particle beam irradiation apparatus of the embodiment 2, the active depth direction irradiation field spread means 15 and 60 and the passive lateral direction irradiation field spread means 50 are combined, and the three-dimensional irradiation system is executed. The active depth direction irradiation field spread means 15 and 60 superimpose plural irradiation layers having different ranges in the irradiation direction of the particle beam PB, that is, in the depth direction, and form the spread-out Bragg peak SOBP in the depth direction. Similarly to the embodiment 1, the bolus 45 makes the irradiation dose to the deepest layer TVd and each of the irradiation layers adjacent thereto substantially constant, and simplifies the control of the irradiation field spread means 15 and 60 in the depth direction.

FIG. 11 shows the structure of an irradiation nozzle 31 used in the particle beam irradiation apparatus of the embodiment 2 of the invention. The irradiation nozzle of FIG. 11 is denoted by symbol 31B. As is apparent from FIG. 11, the irradiation nozzle 31B used in the embodiment 2 includes Wobbler deflection electromagnets 51a and 51b, a scattering plate 58, beam position monitors 52a and 52b to monitor the irradiation position of a particle beam PB, a dose monitor 53 to monitor the irradiation dose of the particle beam PB, a bolus attachment stand 54, a range shifter 56, and a variable collimator 57.

The Wobbler deflection electromagnets 51a and 51b and the scattering plate 58 constitute the passive lateral direction irradiation field spread means 50. The Wobbler deflection electromagnets 51a and 51b scan the particle beam PB in a donut shape, the particle beam BP scanned in the doughnut shape is irradiated to the scattering body 58, and the irradiation field is spread in the lateral direction, that is, on the X, Y plane.

The range shifter 56 constitutes the active depth direction irradiation field spread means 60. The range shifter 56 is inserted so as to cross the particle beam PB, decreases the energy of the particle beam PB according to an adjustment signal supplied thereto, and spreads the irradiation field in the depth direction. The active depth direction irradiation field spread means 60 is also controlled by a control calculator to control the whole apparatus. In the embodiment 2, the active depth direction irradiation field spread means 15 is formed of the energy setting controller 13 to the accelerator 12, and the active depth direction irradiation field spread means 60 is formed of the range shifter 56. By using these, the sufficient irradiation field spread in the depth direction can be obtained. However, one of these can non be used.

The variable collimator 57 is for limiting the irradiation field in the lateral direction, is moved in an arrow A direction by remote control, and adjusts the irradiation field in the lateral direction, that is, on the X, Y plane. As the variable collimator 57, for example, a multilobed collimator is used. The irradiation field in the lateral direction is adjusted by the variable collimator 57, so that the three-dimensional dose distribution is formed.

An arrow PB of FIG. 11 indicates the irradiation direction of the particle beam PB. The Wobbler deflection electromagnets 51a and 51b are disposed to be adjacent to each other at the upstream side in the irradiation direction. The scatterer 58 is disposed between the deflection electromagnet 51b and the beam position monitor 52a. The beam position monitors 52a and 52b are disposed to be spaced from each other in the irradiation direction, and the dose monitor 53 is disposed between the beam position monitors 52a and 52b and near the beam position monitor 52b. The bolus attachment stand 54 is disposed nearest the patient and at the downstream side in the irradiation direction, and a bolus 45 is attached to the bolus attachment stand 54. The range shifter 56 is disposed between the dose monitor 53 and the beam position monitor 52a and near the dose monitor 53. The variable collimator 57 is disposed between the beam position monitor 52b and the bolus attachment stand 54.

In this embodiment 2, the active depth direction irradiation field spread means 15 and 60 and the passive lateral direction irradiation field spread means 50 are combined, and further, the bolus 45 is combined with these. Similarly to the embodiment 1, the bolus 45 makes the dose to the deepest layer TVd and each of the irradiation layers adjacent thereto substantially constant, and simplifies the control of the depth direction irradiation field spread means 15 and 60.

In the embodiment 2, it is important that the superposition of the irradiation doses of the deepest layer TVd of the irradiation target TV in the depth direction and the respective irradiation layers adjacent thereto are controlled as planned. However, since an affected organ moves based on the physiological activity, such as breath or blood flow in the body, of the patient, and the irradiation target TV is also displaced according to this, there is a possibility that an error occurs in the superposition of the irradiation doses. For example, although the position of the liver is periodically displaced mainly in the length direction of the body by the breath, it is also periodically displaced in the thickness direction of the body.

In the irradiation method of the particle beam according to the embodiment 2, irradiation is performed once or more to a specific irradiation layer. As the specific irradiation layer, the deepest layer TVd is selected. Since the irradiation dose given to the deepest layer TVd is 5 to 20 times as large as that of the other irradiation layer, when the irradiation dose to the deepest layer TVd is made accurate, the accuracy of the whole irradiation dose distribution can be improved.

Similarly to the embodiment 1, in the embodiment 2, four reirradiations are performed to the deepest layer TVd in accordance with the irradiation procedure shown in FIG. 9, and as a result, similarly to the explanation with reference to FIG. 10, a more accurate irradiation dose can be irradiated to the deepest layer TVd. In the case where the irradiation is performed only once to a certain irradiation layer such as the deepest layer TVd, there is a danger that an excessive irradiation dose is given in an area 204 by the displacement of the irradiation target TV. However, when irradiation is divided into plural parts by the reirradiation, and the irradiation is performed with the equally divided irradiation dose, the occurrence of the excessive irradiation area 204 can be prevented.

As stated above, in the embodiment 2, the reirradiation is performed once or more to the deepest layer TVd, and the number of times of irradiation is made plural, so that the error of the irradiation dose by the displacement of the target region TV can be reduced.

Incidentally, the dose distribution and the specific numerical values of the weighting described here are an example, and the effect of the invention does not depend on the specific numerical values.

The active depth direction irradiation field spread means 60 based on the range shifter 56 used in the embodiment 2 can also be used for the embodiment 1, together with the active depth direction irradiation field spread means 15 of the embodiment 1. When the active depth direction irradiation field spread means 60 is used in the embodiment 1, the active depth direction irradiation field spread means 15 of the embodiment 1 can be omitted.

Embodiment 3

Next, embodiment 3 of the invention will be described. Since a particle beam irradiation apparatus used for the embodiment 3 is the same as that explained in the embodiment 1 or the embodiment 2, the embodiment 3 of a particle beam irradiation method of the invention will be mainly described in the embodiment 3.

In the embodiment 3, a particle beam PB is irradiated in an irradiation procedure shown in FIG. 12. The control procedure of FIG. 12 is also stored in the storage device of the control calculator to control the whole apparatus. In FIG. 12, respective irradiation layers of from the deepest layer TVd to the second layer, the third layer, . . . , the ninth layer are arranged along the vertical column, the sequence of irradiations of the first, the second, . . . , the fifth is arranged in the horizontal column, and irradiation sequences are written as 1, 2, 3, . . . , 16 at intersection points of the respective irradiation layers and the respective sequence of irradiations. The particle beam PB is executed in order of the irradiation sequences 1, 2, 3, . . . , 16.

In the irradiation procedure of FIG. 12, the first irradiation includes the irradiation of the irradiation sequence 1 to the deepest layer TVd, and the irradiations of the irradiation sequences 2, 3, 4, 5, 6, 7, 8 and 9 to the second layer to the ninth layer. The second irradiation includes the irradiation of the irradiation sequence 10 to the deepest layer TVd, and the irradiations of the irradiation sequences 11 and 12 to the second layer and the third layer. The third irradiation includes the irradiation of the irradiation sequence 13 to the deepest layer TVd, and the irradiation of the irradiation sequence 14 to the second layer. The fourth irradiation includes the irradiation of the irradiation sequence 15 to the deepest layer TVd, and the fifth irradiation includes the irradiation of the irradiation sequence 16 to the deepest layer TVd.

All the four irradiations of the irradiation sequences 10, 13, 15 and 16 are reirradiations to the deepest layer TVd, the two irradiations of the irradiation sequences 11 and 14 are reirradiations to the second layer, and the irradiation of the irradiation sequence 12 is the reirradiation to the third layer.

Each of, in total, five irradiations of the irradiation sequences 1, 10, 13, 15 and 16 to the deepest layer TVd is performed with a dose of ⅕ of a highest irradiation dose RV1 corresponding to the deepest layer TVd, and the total irradiation dose becomes RV1. Each of, in total, three irradiations of the irradiation sequences 2, 11 and 14 to the second layer is performed with a dose of ⅓ of a irradiation dose RV2 necessary for the second layer, and the total irradiation dose becomes RV2. Each of the irradiations of the irradiation sequences 3 and 12 to the third layer is performed with a dose of ½ of an irradiation dose RV3 necessary for third layer, and the total irradiation dose becomes RV3. The irradiation doses RV2 to RV9 for the second layer to the ninth layer are sequentially decreased from the irradiation dose RV1 for the deepest layer TVd, and the irradiation doses RV2 and RV3 for the second layer and the third layer are high as compared with the irradiation doses for the fourth layer to the ninth layer.

As stated above, in the embodiment 3, the reirradiation is performed once or more to the deepest layer TVd, and to the second layer and the third layer having the high irradiation doses subsequently thereto. Even in the case where the irradiation target TV is displaced by the physiological activity such as breath, the irradiation error to the deepest layer TVd, the second layer and the third layer can be reduced.

Incidentally, in the embodiment 2, the active depth direction irradiation field spread and the passive lateral direction irradiation field spread are combined, and further, the bolus 45 is combined. Also in this embodiment 2, similarly to the embodiment 3, reirradiation can also be performed once or more to the deepest layer TVd, the second layer and the third layer.

Embodiment 4

Next, embodiment 4 of the invention will be described. Since a particle beam irradiation apparatus used in this embodiment 4 is the same as that described in the embodiment 1 or the embodiment 2, the embodiment 4 of a particle beam irradiation method of the invention will be mainly described also in the embodiment 4.

In this embodiment 4, a particle beam PB is irradiated in an irradiation procedure shown in FIG. 13. This control procedure is also stored in the storage device of the control calculator to control the whole apparatus. In FIG. 13, respective irradiation layers of from the deepest layer TVd to the second layer, the third layer, . . . , the ninth layer are arranged along the vertical column, the sequence of irradiations of the first, the second, . . . , the fifth is arranged in the horizontal column, and irradiation sequences are written as 1, 2, 3, . . . , 16 at intersection points between the respective irradiation layers and the respective sequence of irradiations. The particle beam PB is executed in order of the irradiation sequences 1, 2, 3, . . . , 16.

In the irradiation procedure of FIG. 13, the first irradiation includes the irradiation of the irradiation sequence 1 to the deepest layer TVd and the irradiations of the irradiation sequences 2, 3, 4, 5, 6, 7, 8 and 9 to the second layer to the ninth layer. The second irradiation includes the irradiation of the irradiation sequence 10 to the deepest layer TVd and the irradiations of the irradiation sequences 14 and 16 to the second layer and the third layer. The third irradiation includes the irradiation of the irradiation sequence 11 to the deepest layer TVd and the irradiation of the irradiation sequence 15 to the second layer. The fourth irradiation includes the irradiation of the irradiation sequence 12 to the deepest layer TVd, and the fifth irradiation includes the irradiation of the irradiation sequence 13 to the deepest layer TVd.

All the irradiations of the irradiation sequences 10, 11, 12 and 13 are reirradiations to the deepest layer TVd, the irradiations of the irradiation sequences 14 and 15 are reirradiations to the second layer, and the irradiation of the irradiation sequence 16 is reirradiation to the third layer.

Each of, in total, five irradiations of the irradiation sequences 1, 10, 11, 12 and 13 to the deepest layer TVd is performed with a dose of ⅕ of a highest irradiation dose RV1 corresponding to the deepest layer TVd, and the total irradiation dose becomes RV1. Each of, in total, three irradiations of the irradiation sequences 2, 14 and 15 to the second layer is performed with a dose of ⅓ of an irradiation dose RV2 necessary for the second layer, and the total irradiation dose becomes RV2. Each of the irradiations of the irradiation sequences 3 and 16 to the third layer is performed with a dose of ½ of an irradiation dose RV3 necessary for the third layer, and the total irradiation dose becomes RV3. The irradiation doses RV2 to RV9 for the second layer to the ninth layer are sequentially decreased from the irradiation dose RV1 for the deepest layer TVd, and the irradiation doses RV2 and RV3 for the second layer and the third layer are high as compared with the irradiation doses for the fourth layer to the ninth layer.

In this embodiment 4, after the four reirradiations of the irradiation sequences 10 to 13 to the deepest layer TVd are completed, the two reirradiations of the irradiation sequences 14 and 15 to the second layer are performed. Further, thereafter, the irradiation of the irradiation sequence 16 to the third layer is performed. Also in this embodiment 4, since the reirradiation is performed once or more to the deepest layer TVd and to the second layer and the third layer having high irradiation doses subsequently thereto, even if the irradiation target TV is displaced by the physiological activity such as breadth, the irradiation error to the deepest layer TVd, the second layer and the third layer having the high irradiation doses can be reduced.

Embodiment 5

Next, embodiment 5 of the invention will be described. Since a particle beam irradiation apparatus used in this embodiment is the same as that explained in the embodiment 1 or the embodiment 2, the embodiment 5 of a particle beam irradiation method of the invention will be mainly described also in the embodiment 5.

In this embodiment 5, a particle beam PB is irradiated in an irradiation procedure shown in FIG. 14. This control procedure is also stored in the storage device of the control calculator to control the whole apparatus. In FIG. 14, respective irradiation layers of from the deepest layer TVd to the second layer, the third layer, . . . , the ninth layer are arranged along the vertical column, and weightings (relative values) to the respective irradiation layers, and next thereto, the sequence of irradiations of the first, the second, . . . , the tenth are arranged in the horizontal columns thereof. Irradiation sequences are written as 1, 2, 3, . . . , 24 at intersection points of the respective irradiation layers and the respective sequence of irradiations. The particle beam PB is performed in order of the irradiation sequences 1, 2, 3, . . . , 24.

In the irradiation procedure of FIG. 14, the first irradiation includes the irradiation of the irradiation sequence 1 to the deepest layer TVd and the irradiations of the irradiation sequences 2, 3, 4, 5, 6, 7, 8 and 9 to the respective layers of from the second layer to the ninth layer. The second irradiation includes the irradiation of the irradiation sequence 10 to the deepest layer TVd and the irradiations of the irradiation sequences 11, 12, 13 and 14 to the respective layers of from the second layer to the fifth layer. The third irradiation includes the irradiation of the irradiation sequence 15 to the deepest layer TVd and the irradiations of the irradiation sequences 16 and 17 to the second layer and the third layer. The forth to the tenth irradiations are respectively irradiations of the irradiation sequences 18, 19, 20, 21, 22, 23 and 24 to the deepest layer TVd.

All the nine irradiations of the irradiation sequences 10, 15 and 18 to 24 are reirradiations to the deepest layer TVd, the two irradiations of the irradiation sequences 11 and 16 are reirradiations to the second layer, and the two irradiations of the irradiation sequences 12 and 17 are reirradiations to the third layer. The irradiations of the irradiation sequences 13 and 14 are respectively reirradiations to the fourth layer and the fifth layer.

Each of, in total, ten irradiations of the irradiation sequences 1, 10, 15 and 18 to 24 to the deepest layer TVd is performed with a dose of $\frac{1}{10}$ of a highest irradiation dose RV1 (weighting of 100) corresponding to the deepest layer TVd, and the total irradiation dose becomes RV1. Each of, in total, three irradiations of the irradiation sequences 2, 11 and 16 to the second layer is performed with a dose of $\frac{1}{3}$ of an irradiation dose RV2 (weighting of 30) necessary for the second layer, and the total irradiation dose becomes RV2. Each of the irradiations of the irradiation sequences 3, 12 and 17 to the third layer is performed with a dose of $\frac{1}{2}$ of an irradiation dose RV3 (weighting of 28) necessary for the third layer, and the total irradiation dose becomes RV3. Each of, in total, two irradiations of the irradiation sequences 4 and 13 to the fourth layer are performed with a dose of $\frac{1}{2}$ of an irradiation dose RV4 (weighting of 22) necessary for the fourth layer, and the total irradiation dose become RV4. Each of, in total, two irradiations of the irradiation sequences 5 and 14 to the fifth layer is performed with a dose of $\frac{1}{2}$ of an irradiation dose RV5 (weighting of 20) necessary for the fifth layer, and the total irradiation dose becomes RV5.

This embodiment 5 is characterized in that the reirradiation, the number of times of which is proportional to the weight, is performed to the deepest layer TVd, and the second layer, the third layer, the fourth layer, and the fifth layer each having a weighting (relative value) of 20 or more. Also in this embodiment 5, even if the irradiation target TV is displaced by the physiological activity such as breadth, the irradiation error to the deepest layer TVd, the second layer, the third layer, the fourth layer, and the fifth layer each having a high irradiation dose can be reduced.

Embodiment 6

Next, embodiment 6 of the invention will be described. Since a particle beam irradiation apparatus used in the embodiment 6 is the same as that explained in the embodiment 1 or the embodiment 2, the embodiment 6 of a particle beam irradiation method of the invention will be mainly described also in the embodiment 6.

In this embodiment 6, a particle beam PB is irradiated in an irradiation procedure shown in FIG. 15. This control procedure is also stored in the storage device of the control calculator to control the whole apparatus. In FIG. 15, respective irradiation layers of from the deepest layer TVd to the second layer, the third layer, . . . , the ninth layer are arranged along the vertical column, and weightings (relative values) to the irradiation layers, and next thereto, the sequence of irradiations of the first, the second, . . . , the tenth are arranged in the horizontal columns thereof. Irradiation sequences are written as 1, 2, 3, . . . , 24 at intersection points of the respective irradiation layers and the respective sequence of irradiations. The particle beam PB is performed in order of the irradiation sequences 1, 2, 3, . . . , 24.

In the irradiation procedure of FIG. 15, the first irradiation includes the irradiation of the irradiation sequence 1 to the deepest layer TVd and the irradiations of the irradiation sequences 2, 3, 4, 5, 6, 7, 8 and 9 to the respective layers of from the second layer to the ninth layer. The second irradiation includes the irradiation of the irradiation sequence 10 to the deepest layer TVd, the irradiation of the irradiation sequence 19 to the second layer, the irradiation of the irradiation sequence 21 to the third layer, the irradiation of the irradiation sequence 23 to the fourth layer, and the 24th irradiation to the fifth layer. The third irradiation includes the irradiation of the irradiation sequence 11 to the deepest layer TVd, and the irradiations of the irradiation sequences 20 and 22 to the second layer and the third layer. The fourth to the tenth irradiations are respectively the irradiations of the irradiation sequences 12 to 24 to the deepest layer TVd.

All the nine irradiations of the irradiation sequences 10 to 18 are reirradiations to the deepest layer TVd, the two irradiations of the irradiation sequences 19 and 20 are reirradiations to the second layer, and the irradiations of the irradiation sequences 21 and 22 are reirradiations to the third layer. The irradiations of the irradiation sequences 23 and 24 are respectively reirradiations to the fourth layer and the fifth layer. The nine reirradiations of the irradiation sequences of 10 to 18 to the deepest layer TVd are first collectively performed, and subsequently to this, the reirradiations of the irradiation sequences 19 and 20 to the second layer are performed. Thereafter, the reirradiations to the third layer, the fourth layer, and the fifth layer are executed.

Each of, in total, ten irradiations of the irradiation sequences 1 and 10 to 18 to the deepest layer TVd are performed with a dose of $\frac{1}{10}$ of a highest irradiation dose RV1 (weighting of 100) corresponding to the deepest layer TVd, and the total irradiation dose becomes RV1. Each of, in total, three irradiations of the irradiation sequences 2, 19 and 20 to the second layer is performed with a dose of $\frac{1}{3}$ of an irradiation dose RV2 (weighting of 30) necessary for the second layer, and the total irradiation dose becomes RV2. Each of, in total, three irradiations of the irradiation sequences 3, 21 and 22 to the third layer is performed with a dose of $\frac{1}{3}$ of an irradiation dose RV3 (weighting of 28) necessary for the third layer, and the total irradiation dose becomes RV3. Each of, in total, two irradiations of the irradiation sequences 4 and 23 to the fourth layer is performed with a dose of $\frac{1}{2}$ of an irradiation dose RV4 (weighting of 22) necessary for the fourth layer, and the total irradiation dose becomes RV4. Each of, in total, two irradiations of the irradiation sequences 5 and 24 to the fifth layer is performed with a dose of $\frac{1}{2}$ of an irradiation dose RV5 (weighting of 20) necessary for the fifth layer, and the total irradiation dose becomes RV5.

This embodiment 6 is characterized in that with respect to the deepest layer TVd, and the second layer, the third layer, the fourth layer, and the fifth layer each having a weighting (relative value) of 20 or more, the reirradiation, the number of times of which is proportional to the weighting, is performed. Also in this embodiment 6, even if the irradiation target TV is displaced by the physiological activity such as breath, the irradiation error to the deepest layer TVd, the second layer, the third layer, the fourth layer, and the fifth layer each having the high irradiation dose can be reduced.

Embodiment 7

Next, embodiment 7 of the invention will be described. In this embodiment 7, the embodiment 7 of a particle beam irradiation apparatus of the invention and the embodiment 7 of a particle beam irradiation method of the invention will be described.

In this embodiment 7, a function is added in which breath measurement of a patient or position detection of an irradiation target is performed, and based on the breath measurement or the position detection of the irradiation target, a breath judgment of the patient is performed, and turning on/off of irradiation of a particle beam PB is controlled.

In this embodiment 7, the particle beam irradiation apparatus of the embodiment 7 shown in FIG. 16 is used. The particle beam irradiation apparatus shown in FIG. 16 includes, in addition to a particle beam generation part 10, a particle beam transport part 20 and a particle beam irradiation part 30, a breath measurement device 71, an irradiation target position detection device 73, a breath judgment calculator 75, and a particle beam treatment safety system 77. The particle beam generation part 10 and the particle beam transport part 20 are the same as those shown in FIG. 4. The particle beam irradiation part 30 includes the particle beam irradiation parts 30A, 30B and 30C of FIG. 4, and as its irradiation nozzle 31, the irradiation nozzle 31A used in the embodiment 1 shown in FIG. 5, or the irradiation nozzle 31B used in the embodiment 2 shown in FIG. 11 is used. In the particle beam irradiation method of the embodiment 7, the irradiation method described in the embodiment 1 to the embodiment 6 is used, and further, the turning on/off of the particle beam PB is controlled. Incidentally, in FIG. 16, a patient 70 is illustrated on a treatment stand 32. The particle beam irradiation part 30 irradiates the particle beam PB from just above the patient 70.

The breath measurement device 71 measures the breath of the patient 70 and outputs a breath signal BS, and what is used in a conventional particle beam treatment apparatus or an X-ray CT can be used. As the breath measurement unit 71, it is possible to use a unit in which a light emitting diode (LED) is attached to the abdominal region or the chest region of the patient 70 and the breath is measured by the displacement of the light emitting position of the light emitting diode, a unit in which a reflecting device is used and the displacement of the body is measured by a laser beam, a unit in which an extensible resistor is attached to the abdominal region of the patient and a change of the electric characteristics is measured, a unit in which the breath of the patient 70 is directly measured, or the like.

The irradiation target position detection device 73 detects the position of the irradiation target TV in the patient 70 and outputs a breath signal BS. As the irradiation target position detection device 73, X-ray sources 731 and 732, and X-ray image acquisition devices 741 and 742 corresponding to these are used. The X-ray sources 731 and 732 irradiate X-rays to the irradiation target TV in the patient 70, and the X-ray image acquisition devices 741 and 742 acquire images of X-rays from the X-ray sources 731 and 732, and detects the position of the irradiation target TV. As the X-ray image acquisition devices 741 and 742, for example, an X-ray television apparatus using an image intensifier, means for measuring a scintillator plate by a CCD camera, or the like is used. With respect to the irradiation target TV, there is a method of burying a small piece of metal, such as gold, as a marker, and it becomes easy to specify the position of the irradiation target TV by using this marker.

Both the breath measurement unit 71 and the irradiation target position detection device 73 detects the displacement of the irradiation target TV due to the breath, and generates the breath signals BS. Both the breath signals BS are inputted to the breath judgment calculator 75. The breath judgment calculator 75 judges, based on the correlation of exhalation/inspiration stored in its storage means, the phase of a breath period in real time from the inputted breath signals BS, and outputs a status signal SS to the particle beam treatment safety system 77. The particle beam treatment safety system 77 supplies control signals CS to the particle beam generation part 10 and the particle beam transport part 20 based on the status signal SS, and performs the turning on/off of the particle beam PB from the particle beam irradiation nozzle 31.

According to the embodiment 7, in synchronization with the breath, the turning on/off of the particle beam PB explained in the embodiment 1 to the embodiment 6 is controlled, and the particle beam irradiation can be performed with higher safety and high accuracy. Incidentally, one of the breath measurement device 71 and the irradiation target position detection unit 73 can be used.

Embodiment 8

Next, embodiment 8 of the invention will be described. In this embodiment 8, the embodiment 8 of a particle beam irradiation apparatus of the invention and the embodiment 8 of a particle beam irradiation method of the invention will be described.

In this embodiment 8, a function is added in which breath measurement of a patient or position detection of an irradiation target is performed, a breath judgment of the patient is made based on the breath measurement or the position detection of the irradiation target, and turning on/off of a particle beam PB is controlled. This embodiment 8 is such that the particle beam treatment safety system 77 in the embodiment 7 is replaced by an irradiation control calculator 80, and an irradiation dose of the irradiated particle beam PB is controlled based on a breath signal BS. The other structure is the same as the embodiment 7.

In this embodiment 8, the particle beam irradiation apparatus of the embodiment 8 shown in FIG. 17 is used. A particle beam generation part 10 and a particle beam transport part 20 shown in FIG. 17 are the same as those shown in FIG. 4. A particle beam irradiation part 30 includes the particle beam irradiation parts 30A, 30B and 30C of FIG. 4. The particle beam irradiation part 30 includes an irradiation nozzle 31. As the irradiation nozzle 31, the irradiation nozzle 31A used in the embodiment 1 shown in FIG. 5, and the irradiation nozzle 31B used in the embodiment 2 shown in FIG. 11 are used. In the particle beam irradiation method of this embodiment 8, in addition to the irradiation method described in the embodiment 1 to the embodiment 6, control of the irradiation dose of the particle beam PB is performed.

In this embodiment 8, the breath phase of a patient 70 and the position of the irradiation target TV corresponding thereto are measured, and the correlation of those is stored in storage means of a breath judgment calculator 75. The breath judgment calculator 75 receives a breath signal BS from one of or both of a breath measurement device 71 and an irradiation target position detection part 73, and outputs in real time a position signal PS to indicate the position of the irradiation target TV corresponding to the breath signal BS.

The irradiation control calculator 80 supplies an irradiation dose control signal RS to indicate an irradiation dose corresponding to the position signal PS to the particle beam irradiation part 30 based on the position signal PS from the breath judgment calculator 75. The particle beam irradiation part 30 adjusts the irradiation dose corresponding to the irradiation target TV based on the position signal PS corresponding to the breath signal BS. For example, in the case where the irradiation target TV is the liver, in case the liver is displaced to move away from the irradiation nozzle 31 to a deep position by 1 cm at a certain phase of breath, the irradiation dose of the particle beam PB is adjusted so that the planned irradiation dose is obtained at this deep position. The irradiation control calculator 80 can also be made the control calculator to control the whole apparatus explained in the embodiment 1 to the embodiment 6.

In this embodiment 8, correspondingly to the displacement of the irradiation target TV due to the breath, the irradiation dose of the particle beam PB explained in the embodiments 1 to 6 is adjusted, and therefore, the irradiation with higher accuracy can be performed. Incidentally, in the embodiment 8, when the breath signal BS from the irradiation target position detection device 73 is used, as compared with the breath signal BS from the breath measurement device 71, the position of the irradiation target TV can be more directly detected, and the irradiation with higher accuracy can be performed.

Embodiment 9

Next, embodiment 9 of the invention will be described. In this embodiment 9, the embodiment 9 of a particle beam irradiation apparatus of the invention and the embodiment 9 of a particle beam irradiation method of the invention will be described.

Although an irradiation target TV of a patient 70 is displaced according to the breath of the patient 70, the displacement is mainly the displacement along a specific axis. With respect to an organ of the chest region and the abdominal region, there are many displacements along the lengthwise direction of the body by the operation of the diaphragm. FIG. 18 shows a state in which the irradiation target TV in the patient 70 is displaced in an arrow C direction along the lengthwise direction of the body.

Although the particle beam PB is irradiated as indicated by an arrow B1 from just above the body in general, when the particle beam PB is irradiated as indicated by an arrow B2 from obliquely above a head 70h of the patient 70, the displacement of the irradiation target TV in the arrow C direction by the breath of the patient 70 can be decomposed into the irradiation direction of the particle beam, PB, that is, the depth direction and the lateral direction perpendicular thereto, and the irradiation error to the irradiation target TV by the breath can be made small.

In the embodiment 9, attention is paid to this, and the particle beam PB explained in the embodiment 1 to the embodiment 6 is irradiated obliquely with respect to the lengthwise direction of the body. In the particle beam irradiation apparatus of the embodiment 9, both a rotation gantry 90 shown in FIGS. 19 and 20 and a treatment stand rotation mechanism are used.

The rotation gantry 90 is a large cylinder and is rotatable around a horizontal axial line 91. A treatment stand 32 is installed inside the rotation gantry 90. The treatment stand 32 is rotated by the treatment stand rotation mechanism around a vertical axial line 92 perpendicular to the horizontal axial line 91. The particle beam irradiation nozzle 31 is installed at an irradiation point P on the peripheral surface of the rotation gantry 90.

FIG. 19 shows a state in which the horizontal axial line 91 and the lengthwise direction of the body become parallel to each other, and the particle beam PB is irradiated just downward from the irradiation point P in an arrow B1 direction. FIG. 20 shows a state in which the rotation gantry 90 is rotated by almost 45 degrees in the counterclockwise direction from FIG. 19 around the horizontal axial line 91, and the treatment stand 32 is rotated by 90 degrees around the vertical axial line 92 from FIG. 19. In the state of FIG. 20, the particle beam PB is irradiated along an arrow B2 obliquely from above the head 70h of the patient 70.

In the particle beam irradiation method of the embodiment 9, since the particle beam PB is irradiated along the arrow B2 obliquely from above the head 70h of the patient 70, the displacement of the irradiation target TV in the arrow C direction by the breath of the patient 70 can be decomposed into the irradiation direction of the particle beam PB, that is, the depth direction and the lateral direction perpendicular thereto, and the irradiation error to the irradiation target TV by the breath can be made small.

INDUSTRIAL APPLICABILITY

The irradiation method of the particle beam of the invention is used as the treatment method for, for example, cancer or the like, and the irradiation apparatus of the particle beam of the invention is used as the treatment apparatus for, for example, cancer or the like.

BRIEF DESCRIPTION OF THE DRAWINGS

[FIG. 6] An explanatory view of a particle beam irradiation method of embodiment 1, in which FIG. 6(a) is a perspective view showing an irradiation target, and FIG. 6(b) is a scanning explanatory view of irradiation spots.

[FIG. 7] An explanatory view of a conventional spot scanning technique, in which FIG. 7(a) is a perspective view showing an irradiation target, and FIG. 7(b) is a scanning explanatory view of irradiation spots.

[FIG. 12] A view showing an irradiation procedure in embodiment 3 of a particle beam irradiation method of the invention.

[FIG. 13] A view showing an irradiation procedure in embodiment 4 of a particle beam irradiation method of the invention.

[FIG. 14] A view stowing an irradiation procedure in embodiment 5 of a particle beam irradiation method of the invention.

[FIG. 15] A view showing an irradiation procedure in embodiment 6 of a particle beam irradiation method of the invention.

DESCRIPTION OF REFERENCE NUMERALS AND SIGNS

Figure 1:
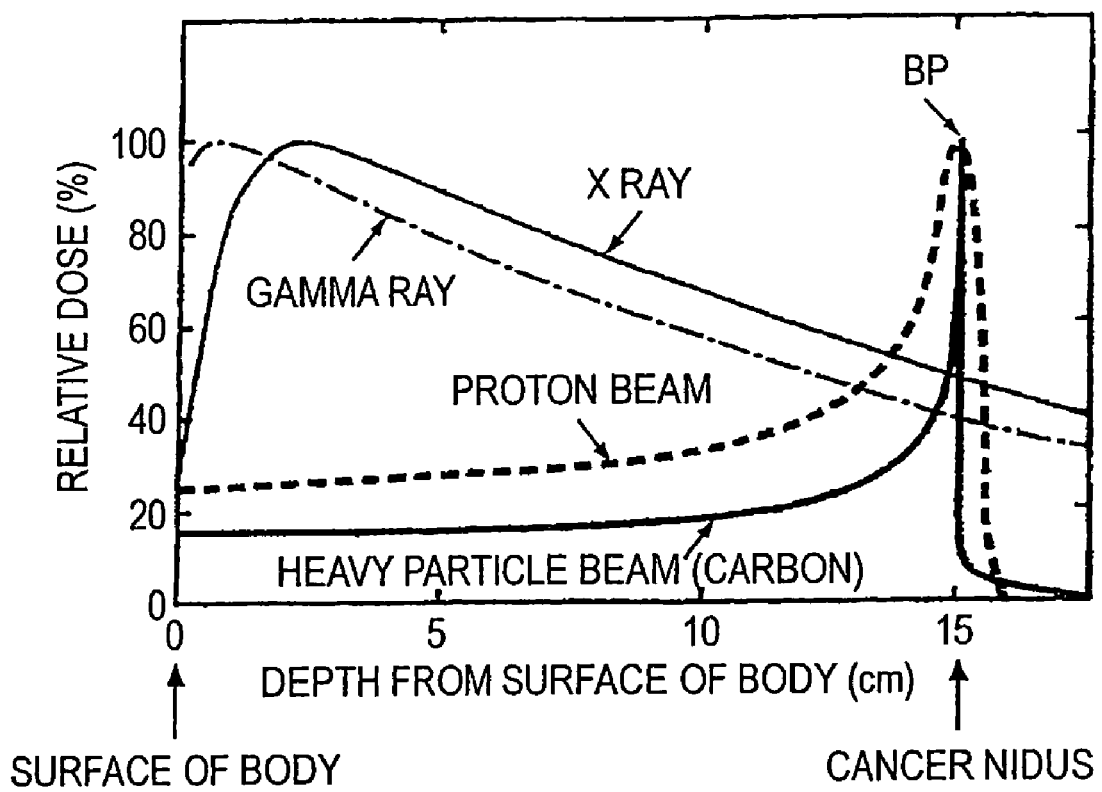
[FIG. 1] A diagram showing dose distributions of various radiation beams in a body.
Figure 2A:
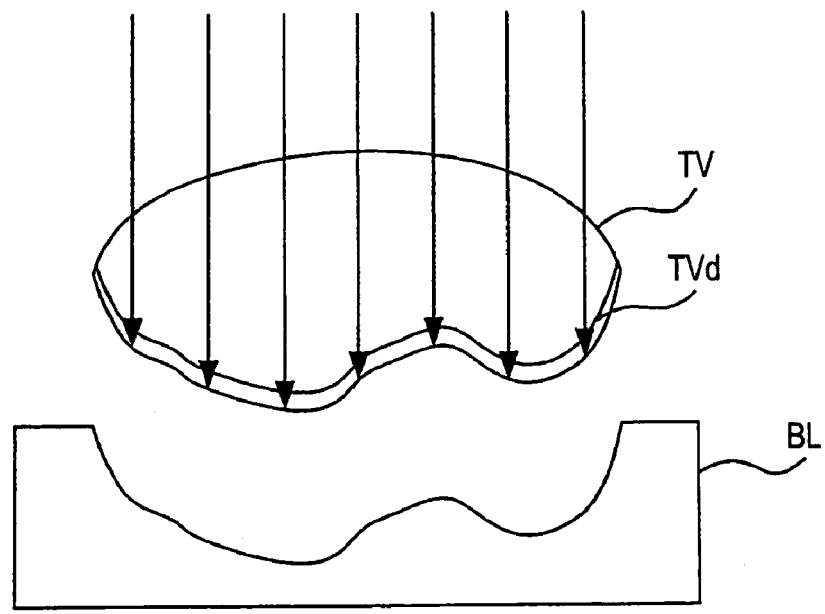
[FIG. 2] An explanation view showing conversion of irradiation energy by a bolus.
Figure 2B:
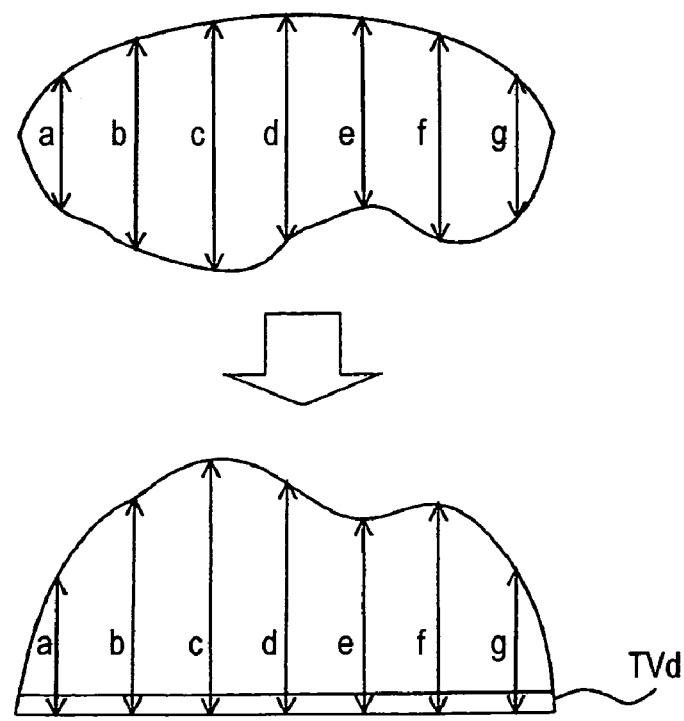
Figure 3:
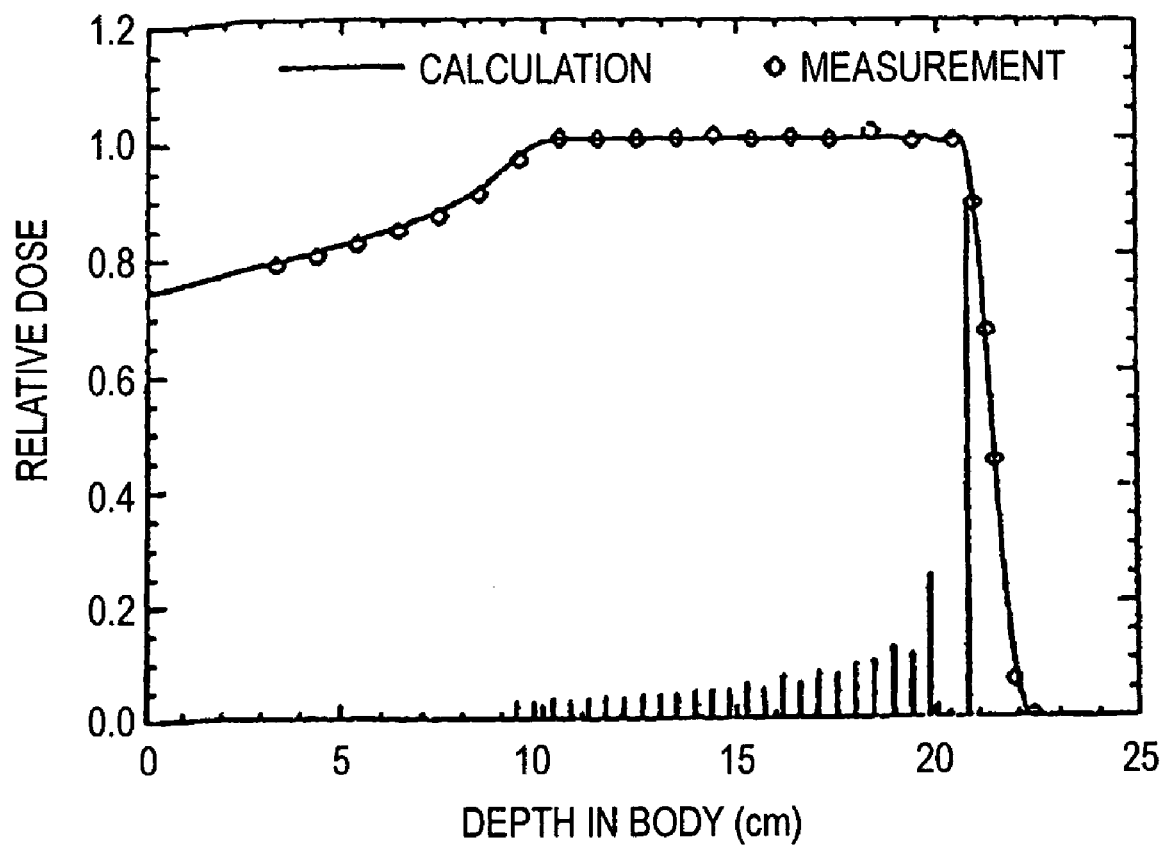
[FIG. 3] A dose distribution view of a particle beam in a body and in a depth direction.
Figure 4:
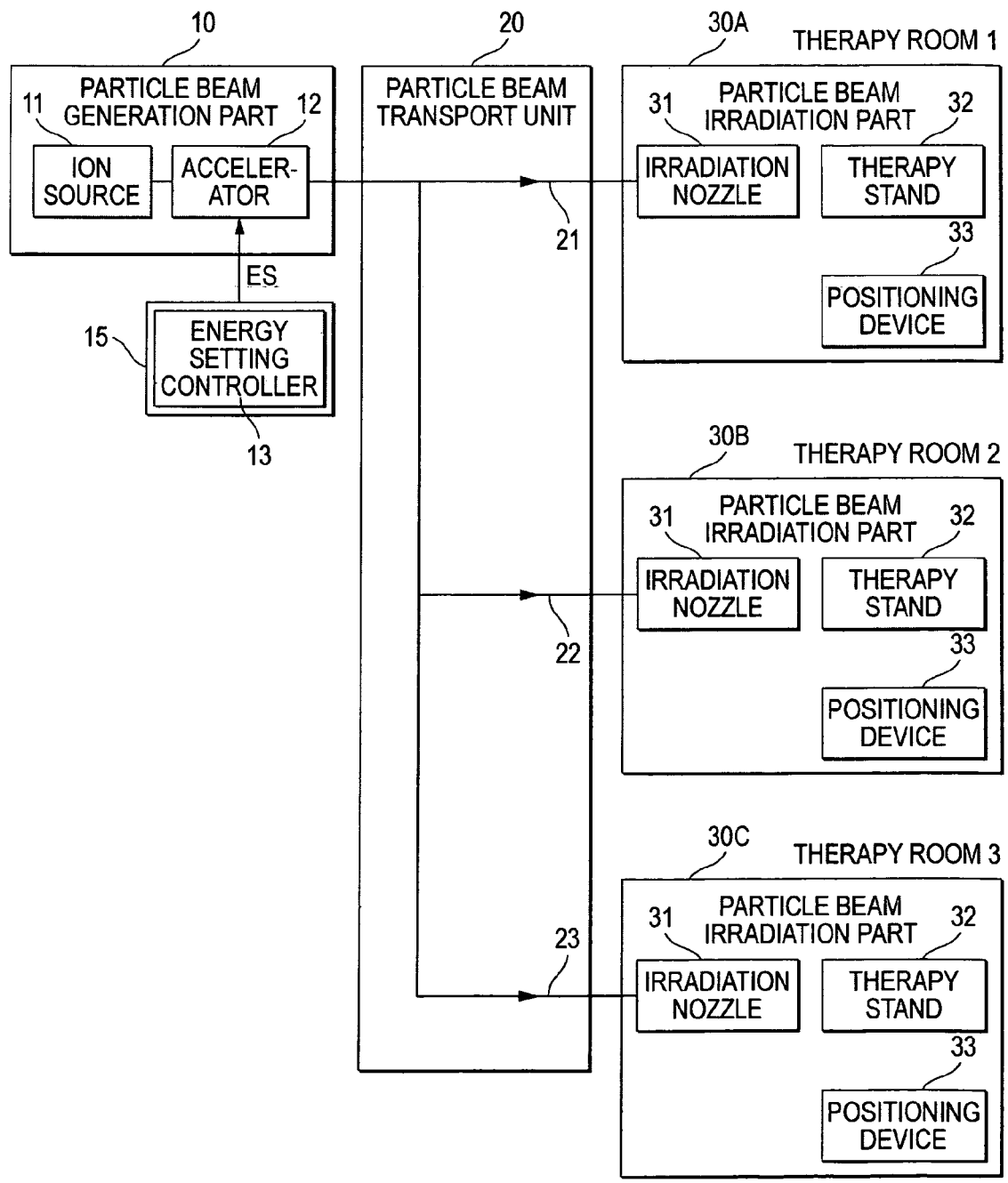
[FIG. 4] A whole structural view of embodiment 1 of a particle beam irradiation apparatus of the invention.
Figure 5:
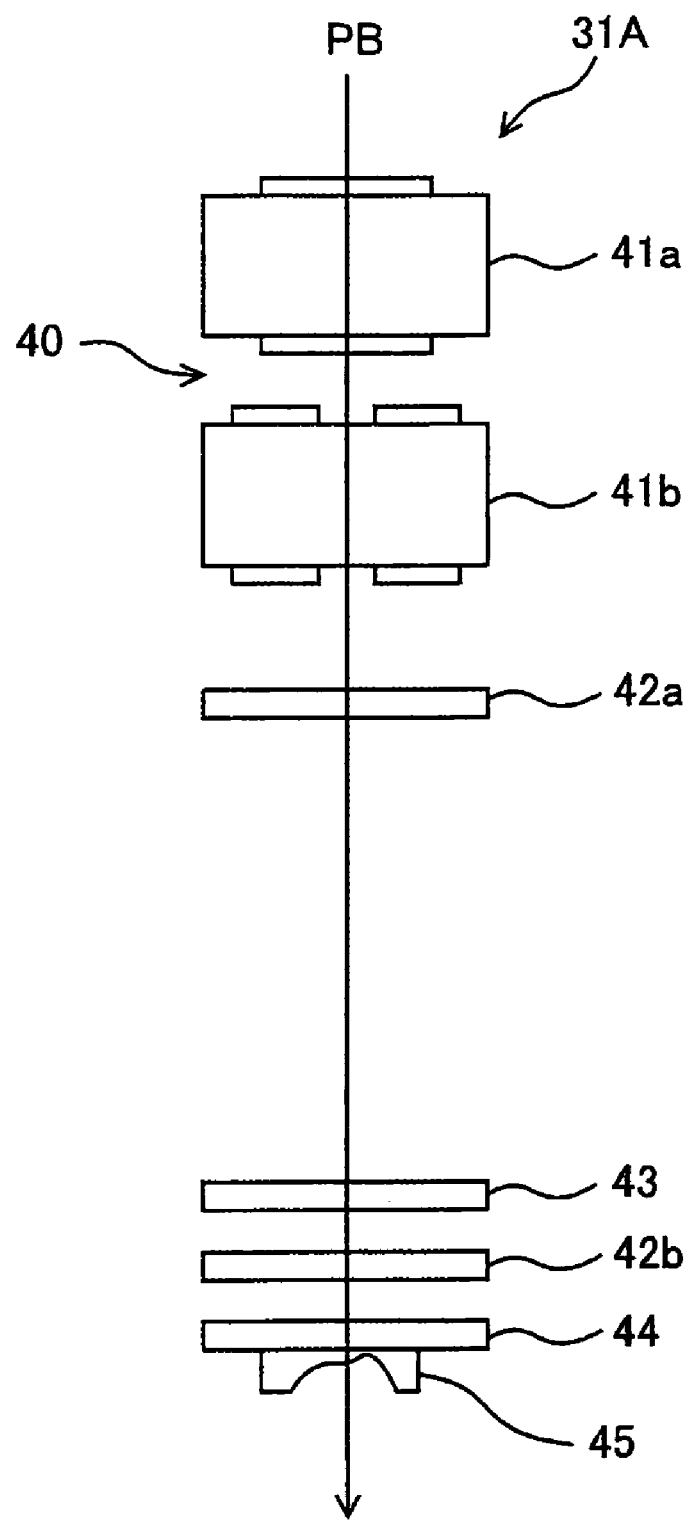
[FIG. 5] An inner structural view of an irradiation nozzle of embodiment 1.
Figures 8, 9:
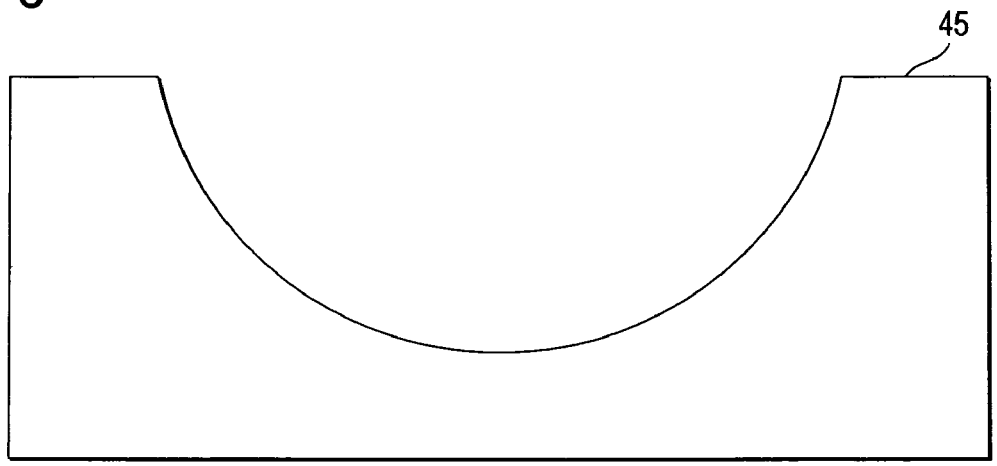
[FIG. 8] A sectional view of a bolus used in the particle beam irradiation method of FIG. 6.
[FIG. 9] A view showing an irradiation procedure in embodiment 1 of the particle beam irradiation method of the invention.
Figure 10:
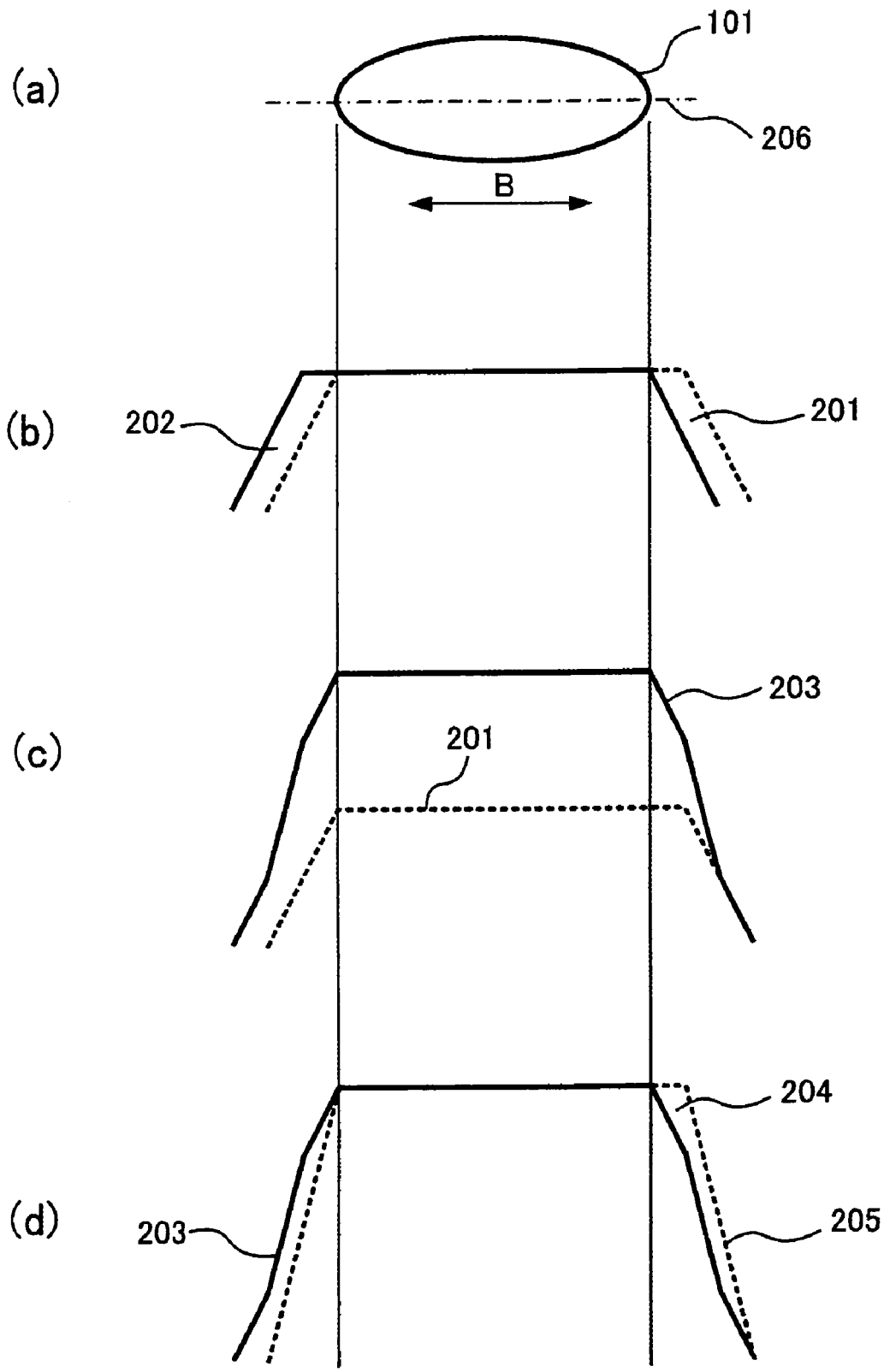
[FIG. 10] A diagram showing an effect of an irradiation procedure of embodiment 1.
Figure 11:
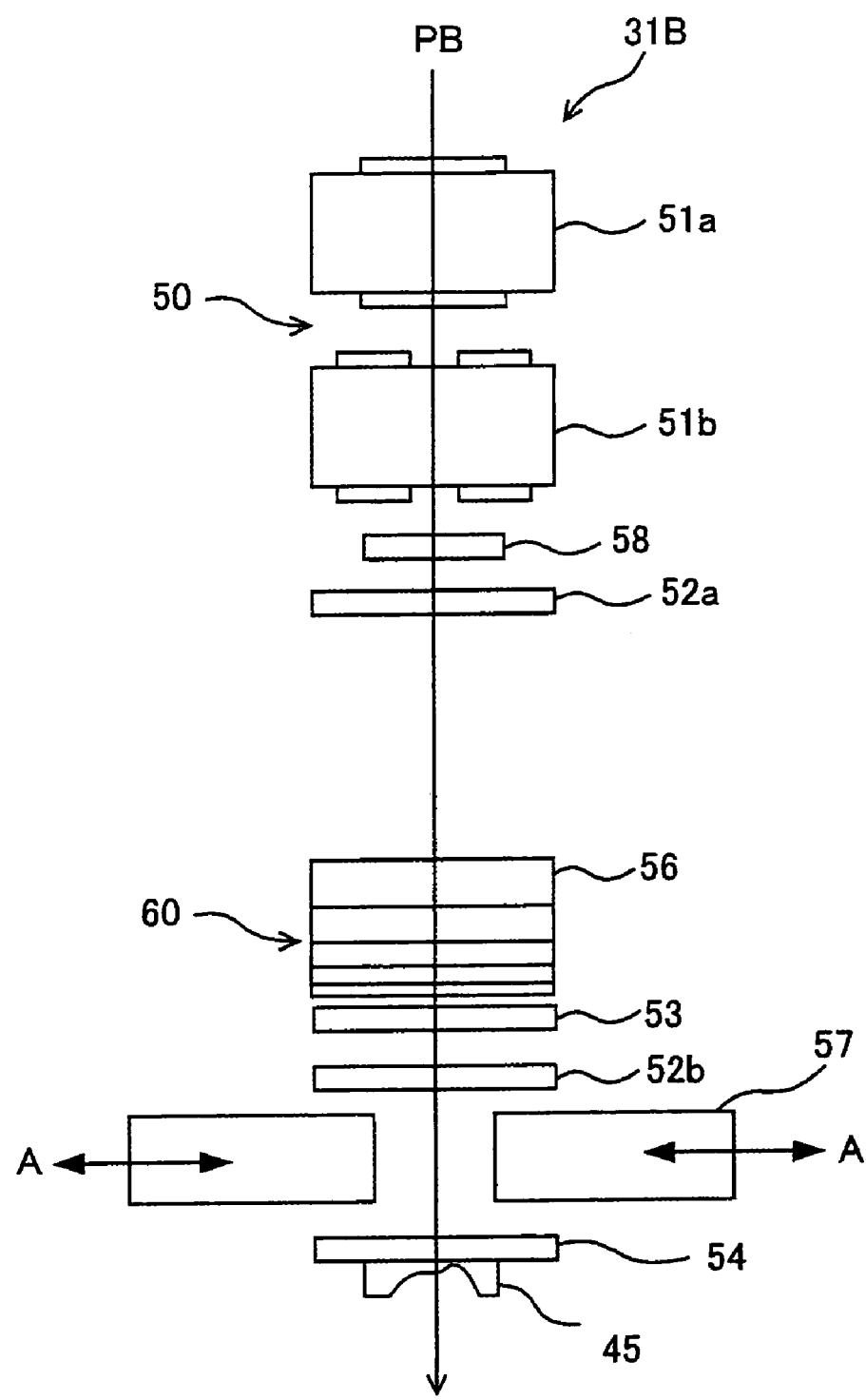
[FIG. 11] An inner structural view of an irradiation nozzle in embodiment 2 of a particle beam irradiation apparatus of the invention.
Figure 16:
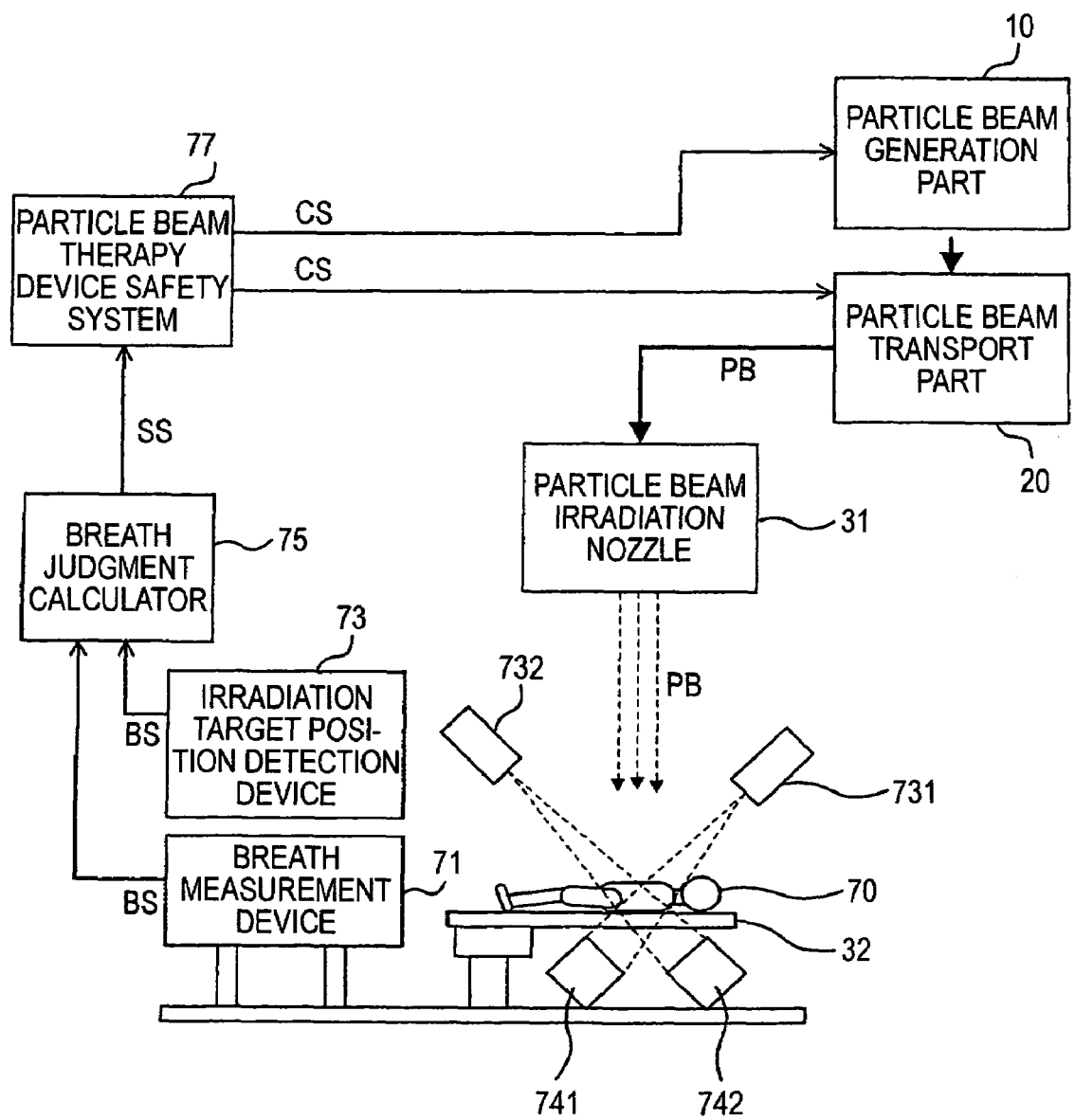
[FIG. 16] A structural view of embodiment 7 of a particle beam irradiation apparatus of the invention.
Figure 17:
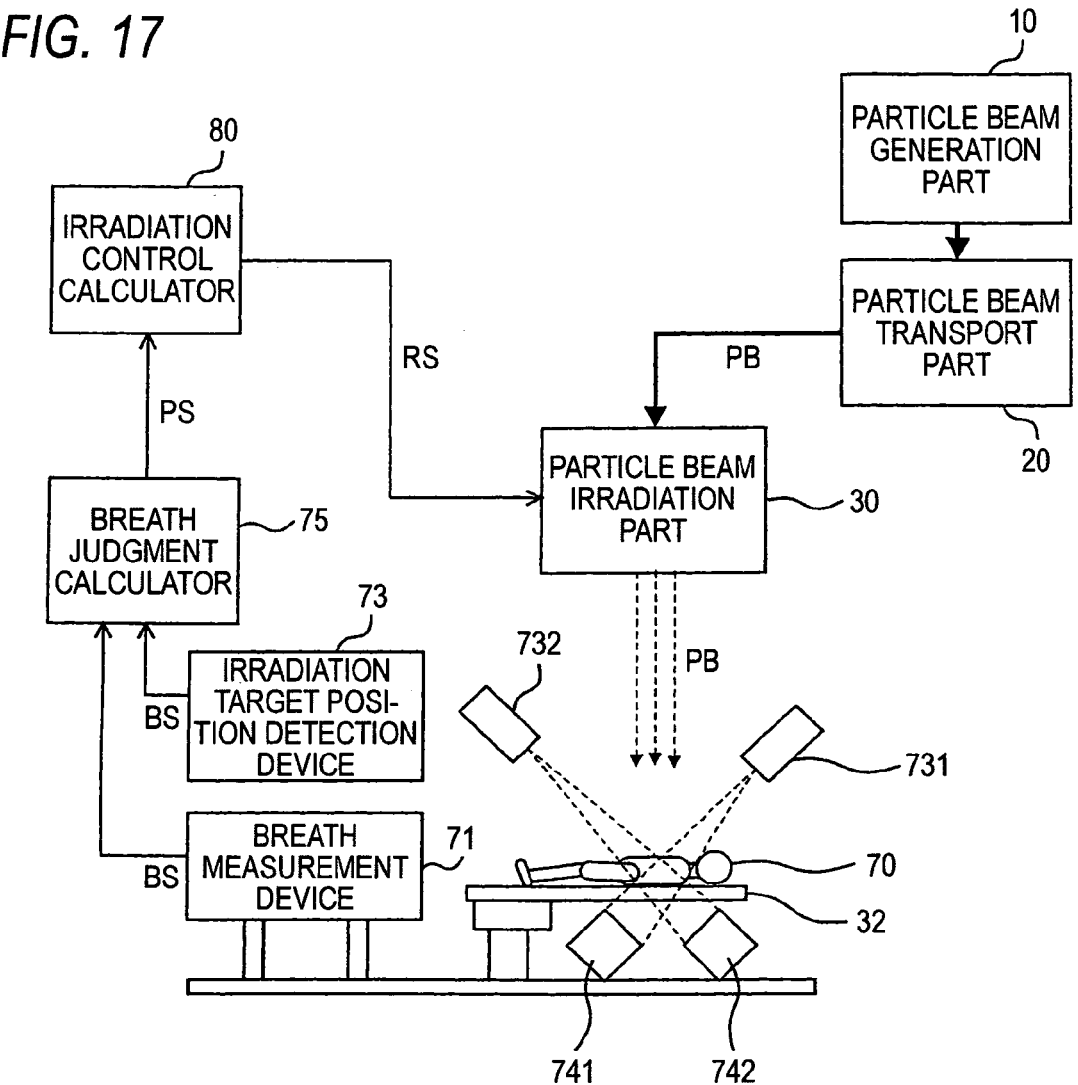
[FIG. 17] A structural view of embodiment 8 of a particle beam irradiation apparatus of the invention.
Figure 18:
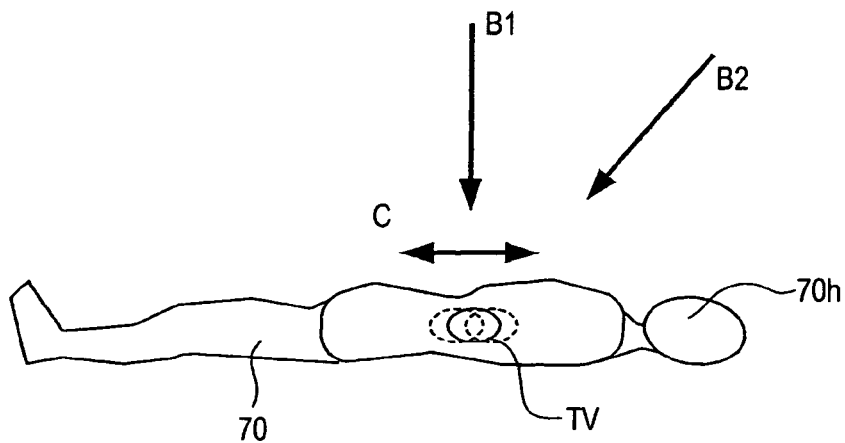
[FIG. 18] An explanatory view of an irradiation direction of a particle beam relating to embodiment 9 of a particle beam irradiation method of the invention.
Figure 19:
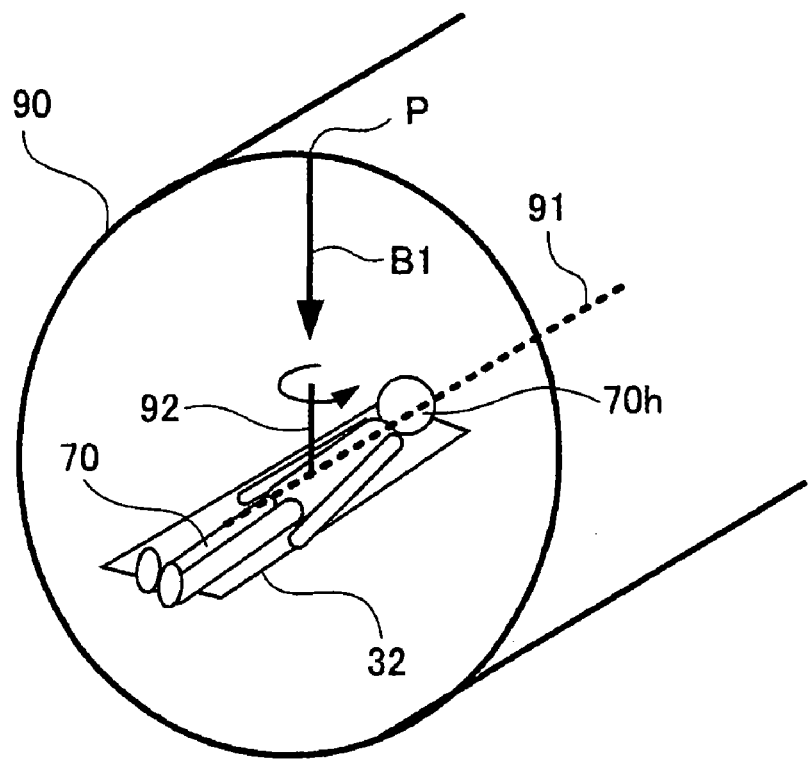
[FIG. 19] A perspective view showing embodiment 9 of a particle beam irradiation apparatus of the invention.
Figure 20:
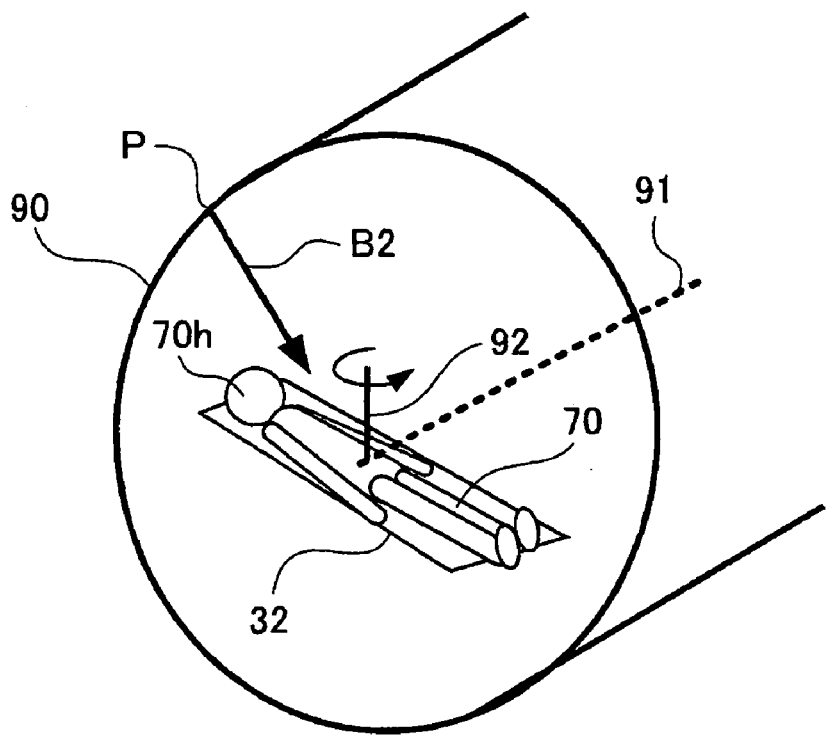
[FIG. 20] A perspective view showing a rotation state of embodiment 9 of the particle beam irradiation apparatus of the invention.

10: particle beam generation part, 12: accelerator, 15, 60: depth direction irradiation field spread means, 20: particle beam transport part, 30, 30A, 30B, 30C: particle beam irradiation part, 31, 31A, 31B: irradiation nozzle, 40: lateral direction irradiation field spread means, TV: irradiation target, TVd: deepest layer, S: irradiation spot, PB: particle beam, 45: bolus, 50: lateral direction irradiation field spread means, 71: breath measurement device, 73: irradiation target position detection device, 75: breath judgment calculator, 77: particle beam treatment device safety system, 80: irradiation control calculator, 90: rotation gantry.

The invention claimed is:

1. A particle beam irradiation method which uses both a depth direction irradiation field spread for spreading an irradiation field of a particle beam in a depth direction along an irradiation direction of the particle beam, and a lateral direction irradiation field spread for spreading the irradiation field of the particle beam in a lateral direction perpendicular to the irradiation direction of the particle beam, and irradiates the particle beam at an irradiation target, the method comprising:
   superimposing plural irradiation layers having different ranges in the irradiation direction of the particle beam, the depth direction irradiation field spread being an active irradiation field spread;
   disposing a bolus having a shape along a deepest part of the irradiation target in the depth direction is disposed to cross the particle beam;
   re-irradiating at least one selected irradiation layer selected from the plural irradiation layers one or more times with the particle beam for irradiating a planned irradiation dose of the particle beam for the one selected irradiation layer, the one selected irradiation layer is a deepest irradiation layer among the plural irradiation layers;
   detecting a displacement of the irradiation target when the irradiation target is displaced; and
   adjusting an irradiation dose of the particle beam according to the displacement of the irradiation target so that the planned irradiation dose of the particle beam for the one selected irradiation layer is obtained, even if the one selected irradiation layer is displaced.

2. The particle beam irradiation method according to claim 1, wherein the lateral direction irradiation field spread is an active irradiation field spread in which irradiation spots of the particle beam are superimposed in the lateral direction.

3. The particle beam irradiation method according to claim 1, wherein the lateral direction irradiation field spread is a passive irradiation field spread.

4. The particle beam irradiation method according to claim 1, wherein the selected irradiation layer is an irradiation layer having a highest irradiation dose in the plural irradiation layers, and the selected irradiation layer is re-irradiated one or more times with the particle beam.

5. The particle beam irradiation method according to claim 1, wherein plural selected irradiation layers are selected from the plural irradiation layers, and each of the plural selected irradiation layers is re-irradiated one or more times with the particle beam, for irradiating each of the planned irradiation dose of the particle beam for each of the plural selected irradiation layers.

6. The particle beam irradiation method according to claim 5, wherein the number of times of reirradiation for each of the plural selected irradiation layers is the number of times corresponding to the planned irradiation dose for each of the selected irradiation layers.

7. The particle beam irradiation method according to claim 1, wherein when the displacement of the irradiation target is detected, turning on/off the irradiation of the particle beam is performed according to the displacement of the irradiation target.

8. The particle beam irradiation method according to claim 1, wherein in a case where the irradiation target is displaced mainly along a specified direction, the particle beam is irradiated to the irradiation target from a direction oblique to the specified direction.

9. A particle beam irradiation apparatus comprising:
   a particle beam generation part for generating a particle beam;
   a particle beam transport part for transporting the particle beam generated by the particle beam generation part;
   a particle beam irradiation part for irradiating the particle beam transported by the particle beam transport part at an irradiation target;
   depth direction irradiation field spread means for spreading an irradiation field of the particle beam in a depth direction along an irradiation direction of the particle beam;
   lateral direction irradiation field spread means for spreading the irradiation field of the particle beam in a lateral direction perpendicular to the irradiation direction of the particle beam, wherein
      the depth direction irradiation field spread means is an active depth direction irradiation field spread means for superimposing plural irradiation layers having different ranges in the irradiation direction of the particle beam, and
   wherein the particle beam irradiation apparatus further comprises:
      a bolus having a shape along a deepest part of the irradiation target in the depth direction is disposed to cross the particle beam;
      means for re-irradiating the particle beam to at least one selected irradiation layer selected from the plural irradiation layers one or more times with the particle beam for irradiating a planned irradiation dose of the particle beam for the one selected irradiation layer, the one selected irradiation layer is a deepest irradiation layer among the plural irradiation layers;
   displacement detection means for detecting a displacement of the irradiation target; and adjustment means for adjusting an irradiation dose of the particle beam according to the displacement of the irradiation target so that the planned irradiation dose of the particle beam for the one selected irradiation layer is obtained, even if the one selected irradiation layer is displaced.

10. The particle beam irradiation apparatus according to claim 9, wherein the active depth direction irradiation field spread means is coupled to an accelerator for accelerating the particle beam, and for changing an acceleration energy of the particle beam.

11. The particle beam irradiation apparatus according to claim 9, wherein the active depth direction irradiation field spread means is a range shifter disposed to cross the particle beam, and the range shifter adjusts energy of the particle beam according to a given adjustment signal.

12. The particle beam irradiation apparatus according to claim 9, wherein the lateral direction irradiation field spread means is an active irradiation field spread means for superimposing irradiation spots of the particle beam in the lateral direction.

13. The particle beam irradiation apparatus according to claim 9, wherein the lateral direction irradiation field spread means is a passive irradiation field spread means.

14. The particle beam irradiation apparatus according to claim 9, wherein the particle beam irradiation apparatus further comprises a displacement detection means for detecting a displacement of the irradiation target, and a turning on/off means for turning on/off irradiation of the particle beam, wherein the particle beam is turned on/off according to the displacement of the irradiation target.

15. The particle beam irradiation apparatus according to claim 9, wherein the particle beam irradiation part includes an irradiation nozzle to irradiate the particle beam, the irradiation nozzle is mounted on a rotation gantry, and in a case where the irradiation target is displaced mainly along a specified direction, the particle beam is irradiated to the irradiation target from a direction oblique to the specified direction.

* * * * *